US006591472B1

United States Patent
Noone et al.

(10) Patent No.: US 6,591,472 B1
(45) Date of Patent: Jul. 15, 2003

(54) MULTIPLE SEGMENT CATHETER AND METHOD OF FABRICATION

(75) Inventors: Michael S. Noone, Londonderry, NH (US); Albert H. Dunfee, Byfield, MA (US); Matthew S. Poole, Danvers, MA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/207,644

(22) Filed: Dec. 8, 1998

(51) Int. Cl.⁷ ................................................. B23P 17/00
(52) U.S. Cl. .................... 29/417; 29/527.2; 264/171.13; 264/171.18; 604/523
(58) Field of Search .............................. 29/417, 527.2, 29/460; 264/103, 171.12, 171.13, 171.16, 171.17, 171.18, 171.27; 604/523, 524, 526, 527

(56) References Cited

U.S. PATENT DOCUMENTS

| | | | | |
|---|---|---|---|---|
| 4,283,447 A | | 8/1981 | Flynn ........................... 428/36 |
| 4,321,226 A | | 3/1982 | Markling .................... 264/139 |
| 4,385,635 A | * | 5/1983 | Ruiz ........................... 128/658 |
| 4,464,176 A | | 8/1984 | Wijayarathna .............. 604/164 |
| 4,531,943 A | | 7/1985 | van Tassel et al. ......... 604/280 |
| 4,551,292 A | | 11/1985 | Fletcher et al. ............. 264/139 |
| 4,563,181 A | | 1/1986 | Wijayarathna et al. ..... 604/280 |
| 4,577,543 A | * | 3/1986 | Wilson ........................... 87/11 |
| 4,596,563 A | * | 6/1986 | Pande ........................ 604/264 |
| 4,636,346 A | | 1/1987 | Gold et al. |
| 4,665,604 A | * | 5/1987 | Dubowik ...................... 29/415 |
| 4,739,768 A | | 4/1988 | Engelson .................... 128/658 |
| 4,753,765 A | * | 6/1988 | Pande ........................ 264/149 |
| 4,764,324 A | * | 8/1988 | Burnham .................... 264/103 |

(List continued on next page.)

FOREIGN PATENT DOCUMENTS

| | | |
|---|---|---|
| EP | 0 303 487 | 2/1989 |
| EP | 0 555 088 A2 | 8/1993 |
| EP | 0 823 262 A2 | 2/1998 |
| EP | 0 841 072 A2 | 5/1998 |

*Primary Examiner*—Gregory Vidovich
*Assistant Examiner*—Essama Omgba
(74) *Attorney, Agent, or Firm*—Sterne, Kessler, Goldstein & Fox P.L.L.C.

(57) ABSTRACT

Methods of fabricating medical vascular catheters adapted to be inserted into a blood vessel from an incision through the skin of a patient for introducing other devices or fluids for diagnostic or therapeutic purposes and particularly methods for fabricating such catheters with catheter bodies having catheter sections of differing flexibility are disclosed. Such catheter bodies having a proximal catheter body end and a distal catheter body end and formed of a proximal section and at least one distal section that have differing flexibilities are formed in a process comprising the steps of: (1) forming a continuous tubular inner jacket preferably of an inner liner and a reinforcement layer; (2) forming initial layer segments having an initial layer thickness along the length of the inner jacket from a material of first durometer hardness, whereby each initial layer segment is separated by a separation distance: (3) forming a final layer of a material of second durometer hardness with a second layer thickness over the tubular inner jacket along the separation distances and over and/or against the proximal and distal initial layer ends of the initial layer segments to form a continuous catheter body tubing; (4) severing the continuous catheter body tubing into catheter body lengths including a proximal catheter section formed of the material of second hardness and a distal catheter section of the material of first hardness; and (5) completing the catheter fabrication at the proximal catheter body end and the distal catheter body end. Centerless grinding of the catheter body or body tubing, formation of Intermediate catheter body sections, distal soft tips, and discontinuities in the reinforcement layer formed prior to step (2) are also disclosed.

25 Claims, 16 Drawing Sheets

U.S. PATENT DOCUMENTS

| | | | | | |
|---|---|---|---|---|---|
| 4,817,613 | A | | 4/1989 | Jaraczewski et al. | 128/658 |
| 4,863,442 | A | * | 9/1989 | DeMello et al. | 604/282 |
| 5,078,702 | A | | 1/1992 | Pomeranz | 604/280 |
| 5,178,158 | A | | 1/1993 | de Toledo | 128/772 |
| 5,221,270 | A | | 6/1993 | Parker | 604/282 |
| 5,234,416 | A | | 8/1993 | Macaulay et al. | 604/282 |
| 5,279,596 | A | * | 1/1994 | Castaneda et al. | 604/282 |
| 5,334,171 | A | * | 8/1994 | Kaldany | 604/282 |
| 5,336,205 | A | | 8/1994 | Zenzen et al. | 604/280 |
| 5,437,632 | A | * | 8/1995 | Engelson | 604/53 |
| 5,456,674 | A | * | 10/1995 | Bos et al. | 604/280 |
| 5,484,565 | A | * | 1/1996 | Larsen et al. | 264/230 |
| 5,496,294 | A | * | 3/1996 | Hergenrother et al. | 604/282 |
| 5,509,910 | A | | 4/1996 | Lunn | 604/282 |
| 5,538,510 | A | * | 7/1996 | Fontirroche et al. | 604/265 |
| 5,542,924 | A | * | 8/1996 | Snoke et al. | 604/95 |
| 5,545,149 | A | | 8/1996 | Brin et al. | 604/265 |
| 5,584,821 | A | * | 12/1996 | Hobbs et al. | 604/280 |
| 5,599,326 | A | * | 2/1997 | Carter | 604/282 |
| 5,614,136 | A | * | 3/1997 | Pepin et al. | 264/40.3 |
| 5,658,263 | A | * | 8/1997 | Dang et al. | 604/280 |
| 5,674,197 | A | * | 10/1997 | Van Muiden et al. | 604/95 |
| 5,676,659 | A | | 10/1997 | McGurk | 604/282 |
| 5,738,742 | A | * | 4/1998 | Stevens | 156/149 |
| 5,769,830 | A | * | 6/1998 | Parker | 604/282 |
| 5,772,641 | A | | 6/1998 | Wilson | 604/280 |
| 5,836,925 | A | * | 11/1998 | Slotesz | 604/280 |
| 5,851,464 | A | * | 12/1998 | Davila et al. | 264/103 |
| 5,860,963 | A | * | 1/1999 | Azam et al. | 604/280 |
| 5,868,718 | A | * | 2/1999 | Pepin et al. | 604/264 |
| 5,876,386 | A | * | 3/1999 | Samson | 604/282 |
| 5,888,436 | A | * | 3/1999 | Keith et al. | 264/103 |
| 5,891,112 | A | * | 4/1999 | Samson | 604/282 |
| 5,891,114 | A | * | 4/1999 | Chien et al. | 604/282 |
| 5,897,537 | A | * | 4/1999 | Berg et al. | 604/282 |
| 5,902,287 | A | * | 5/1999 | Martin | 604/280 |
| 5,908,413 | A | * | 6/1999 | Lange et al. | 604/529 |
| 5,911,715 | A | * | 6/1999 | Berg et al. | 604/525 |
| 5,916,208 | A | * | 6/1999 | Luther et al. | 604/508 |
| 5,922,443 | A | * | 7/1999 | Larsen et al. | 428/217 |
| 5,938,653 | A | * | 8/1999 | Pepin | 604/527 |
| 5,951,539 | A | * | 9/1999 | Nita et al. | 604/526 |
| 5,971,975 | A | * | 10/1999 | Mills et al. | 604/527 |
| 5,972,143 | A | * | 10/1999 | Stevens | 156/149 |
| 5,976,120 | A | * | 11/1999 | Chow et al. | 604/525 |
| 6,077,258 | A | * | 6/2000 | Lange et al. | 604/527 |
| 6,106,510 | A | * | 8/2000 | Lunn et al. | 604/525 |
| 6,165,166 | A | * | 12/2000 | Samuelson et al. | 604/254 |
| 6,171,296 | B1 | * | 1/2001 | Chow | 604/525 |
| 6,197,015 | B1 | * | 3/2001 | Wilson | 604/524 |
| 6,217,565 | B1 | * | 4/2001 | Cohen | 604/525 |
| 6,217,566 | B1 | * | 4/2001 | Ju et al. | 604/526 |
| 6,245,053 | B1 | * | 6/2001 | Benjamin | 604/523 |
| 6,296,631 | B2 | * | 10/2001 | Chow | 604/525 |

(List continued on next page.)

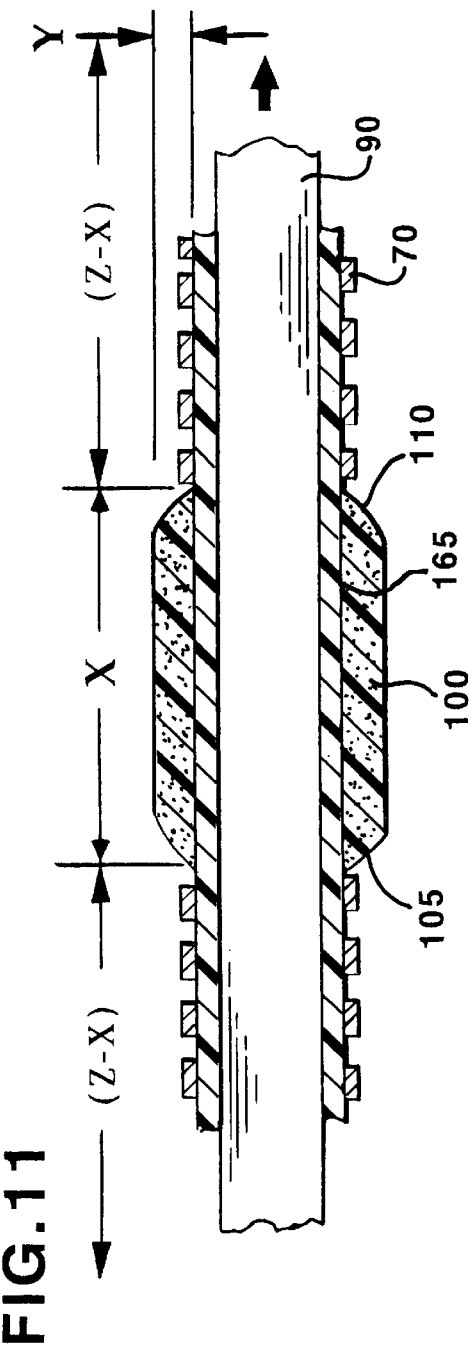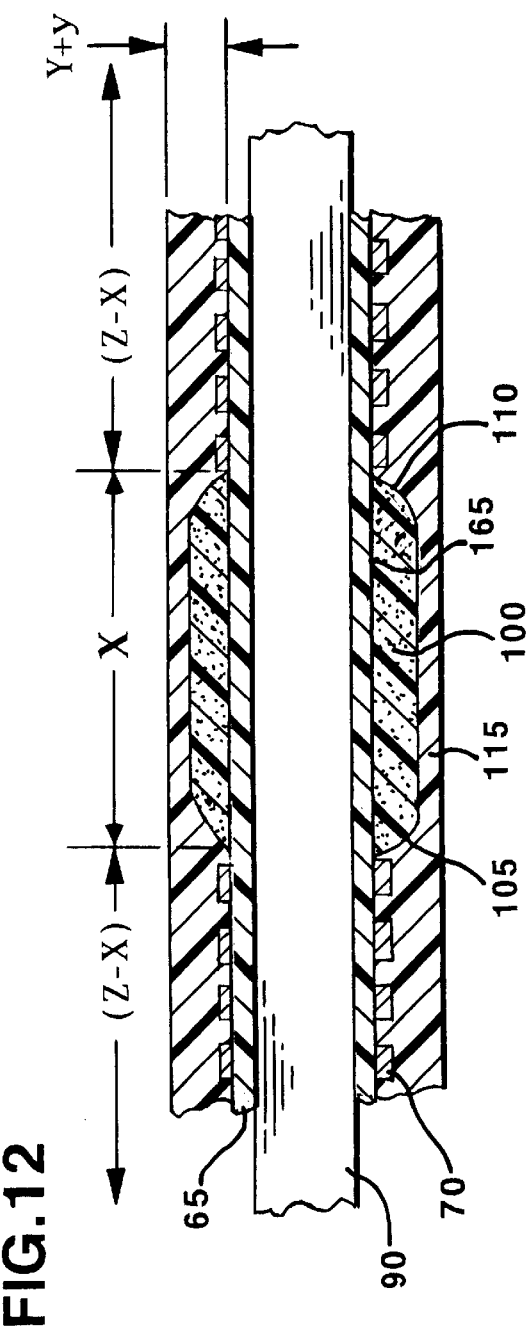
FIG.11
FIG.12

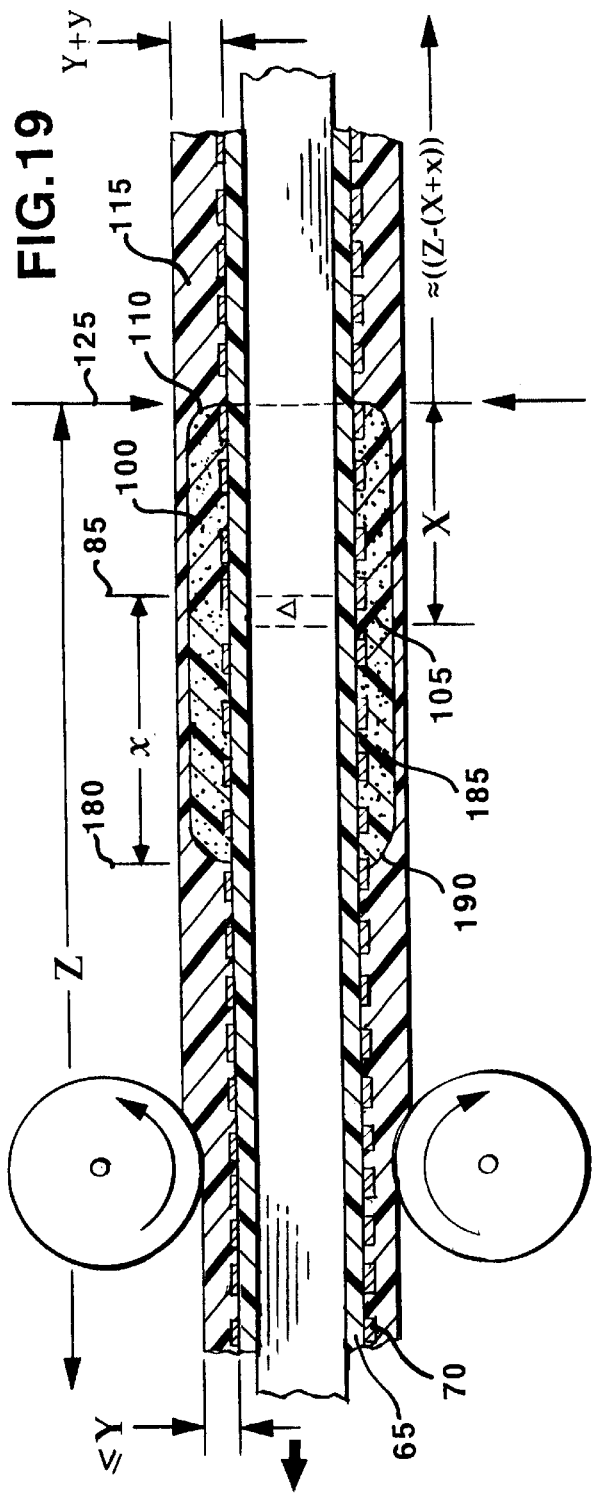

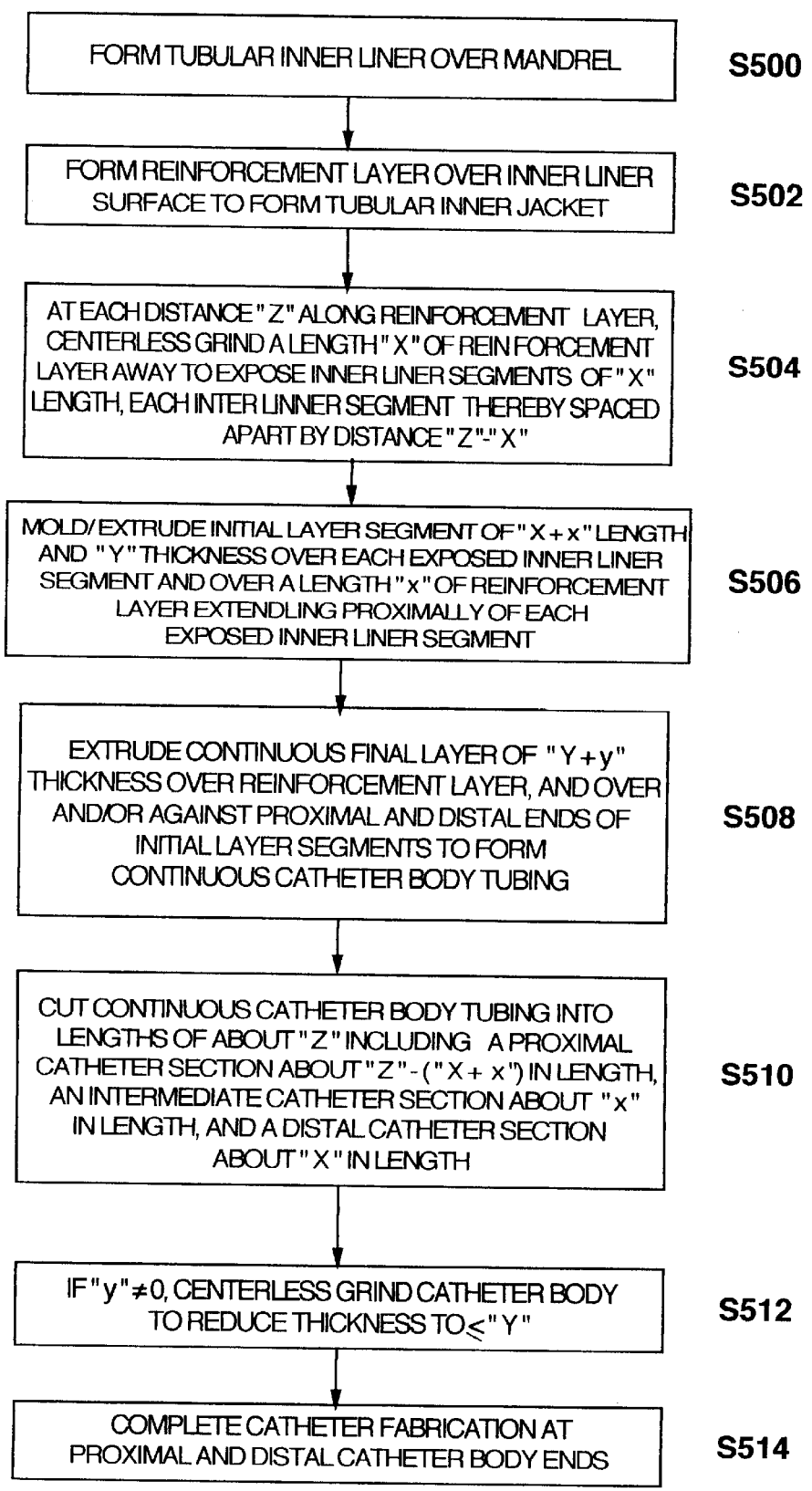

MULTIPLE SEGMENT CATHETER AND METHOD OF FABRICATION

CROSS-REFERENCE TO RELATED PENDING APPLICATIONS

Reference is made to commonly assigned U.S. patent application Ser. No. 09/046,241 filed Mar. 23, 1998, for CATHETER HAVING EXTRUDED RADIOPAQUE STRIPES EMBEDDED IN SOFT TIP AND METHOD OF FABRICATION, in the names of Nasser Rafiee. et al.

FIELD OF THE INVENTION

The present invention relates to methods of fabricating medical vascular catheters adapted to be inserted into a blood vessel from an incision through the skin of a patient for introducing other devices or fluids for diagnostic or therapeutic purposes and particularly methods for fabricating such catheter bodies with catheter sections of differing flexibility.

BACKGROUND OF THE INVENTION

Catheters are tube-like medical instruments that are inserted into a body cavity, duct, tract, organ or blood vessel for a wide variety of diagnostic or therapeutic reasons, including delivery of diagnostic radiopaque materials, infusion of therapeutic drugs, performance of other interventional procedures, drainage of body cavities, organs or vessels, perfusion, and the like. Medical vascular catheters for each of these purposes can be introduced to numerous target sites within a patient's body by guiding the catheter through an incision made in the patient's skin and a blood vessel and then through the vascular system to the target site. Certain vascular catheters are introduced over a previously introduced guide wire or infusion wire and/or within a previously introduced guiding catheter or are advanced by blood flow in the vessel.

Medical vascular catheters generally comprise an elongated, flexible catheter tube or body with a catheter side wall enclosing a catheter lumen extending between a proximal catheter body end coupled to a relatively more rigid catheter hub to a distal catheter body end. The catheter body may be relatively straight or inherently curved or curved by insertion of a curved stiffening wire or guide wire through the catheter lumnen. The catheter body and catheter side wall are typically fabricated and dimensioned to minimize the catheter body outer diameter and side wall thickness and to maximize the catheter lumen diameter while retaining sufficient side wall flexibility and strength characteristics to enable the catheter to be used for the intended medical purpose.

Such medical catheters may be designed and used for diagnostic or therapeutic purposes in a wide range of catheter body sizes, lengths and configurations for accessing relatively large blood vessels, tracts, ducts or organs of the body or relatively small cardiac, neural or peripheral blood vessels that are frequently tortuous.

Guiding catheters are used to access a site in a patient's body and are formed to have a high degree of directional control and to provide a guiding catheter lumen through which smaller diameter, therapeutic catheters having little or no directional control are advanced to the site. In the field of vascular intervention, guiding catheters are particularly useful to guide angioplasty and atherectomy catheters through the vasculature to a site of a blockage, such as, coronary, cerebral and renal sites. Typically guiding catheters have a specific distal section shape adapted and sized to facilitate insertion to the site of interest.

The requirements of a good guiding catheter include high torque transmission and pushability for advancement through the vasculature, high catheter lumen lubricity to facilitate insertion of catheters and other devices therethrough, low kinking characteristics, and good distal shape memory. Additionally it is desirable to provide a smooth and relatively soft distal tip leading surface to prevent damage to the vascular vessels during advancement. It is also desirable to provide a radiopaque marker near the distal tip of the catheter to enhance its visibility by fluoroscopy. A wide variety of guiding catheters have been developed that address these design requirements as set forth for example in U.S. Pat. No. 4,817,613 to Jaraczewski et al. A number of distal soft tips and radiopaque markers are also described in the above-referenced, commonly assigned, '241 patent application and in commonly assigned U.S. Pat. Nos. 5,509,910 to Lunn and 5,545,149 to Brin et al. and in U.S. Pat. Nos. 4,283,447 to Flynn, 5,078,702 to Pomeranz, 5,234,416 to Macauley et al. and 5,221,270 to Parker.

Such guiding catheter bodies are typically formed with relatively long and stiff proximal sections or shafts and relatively short and soft distal tips, although short intermediate bonding segments or sections can be employed to assist bonding the soft distal tip to,the distal end of the proximal shaft as disclosed in the above-referenced '910 and '149 patents. Typically, the proximal section or shaft is formed of an inner tube, metal or polymeric filaments braided overlying the inner tube, and an outer tube over the braid, thereby providing a reinforced catheter shaft as disclosed in the above-referenced '910, '416, and '149 patents. The distal soft tip is either formed separately and adhered to the distal end of the catheter shaft through a variety of techniques or is formed integrally as an extension of one of the outer or inner liners as disclosed in the above-referenced '613 patent, for example. Butt welding techniques are disclosed in the above-referenced '910, '416, and '149 patents, and lap joint techniques are disclosed in U.S. Pat. Nos. 4,531,943 to Van Tassel et al. and 4,551,292, issued to Fletcher et al. and in the above-referenced '270 patent The exterior surface of the distal end of the catheter shaft is ground circumferentially using a "centerless" grinder to reduce the distal shaft wall thickness. The tip member is then fitted over the distal end of the catheter shaft to form a lap joint with the distal shaft and is then bonded to the distal shaft using an adhesive or other bonding technique.

Angiographic catheters of the type disclosed in U.S. Pat. No. 5,738,742 to Stevens are also formed with a wire braid reinforced proximal catheter section or shaft and a distal soft tip that is attached-thereto. In one approach characterized as prior art, a distal end portion of the proximal catheter shaft is centerless ground to a shape accommodating attachment of a separately formed soft distal tip that is then attached thereto. In a further approach presented by Stevens, a continuous reinforced tubing is first fabricated wherein an inner tube is formed over a mandrel, wire braid is applied over the inner tube outer wall during a continuous fabrication process, periodic sections of the wire braid are centerless ground away to expose the inner tube in those sections, and a continuous elastomeric coating is applied over the wire braid and exposed inner tube sections. The continuous reinforced tubing is cut to catheter body lengths including the sections without the wire braid, and the outer layer and inner layer of the section without wire braid are thermally fused together and shaped to form an integral soft distal tip. A very similar technique is disclosed in U.S. Pat. No.

4,321,226 to Markling for fabrication of catheters of unspecified types. Other angiographic catheters employ relatively stiff polymeric materials, e.g., certain nylon blends, polyamides, polyesters, etc., to provide a relatively rigid proximal catheter shaft and other softer blends of like materials in the distal end section or distal soft tip as disclosed, for example, in U.S. Pat. No. 4,563,181 to Wijayarathna et al.

Small diameter medical catheters or "microcatheters" having a catheter body outer diameter in the range of one, French (1F; 0.33 mm) to three French (3F; 1.00 mm), are typically used in tortuous vascular passageways for diagnostic and interventional neurological techniques, such as the imaging and treatment of aneurysms, tumors, arteriovenous malformations/fistulas, and the like, in the blood vessels in the brain. Such neurological catheters must be very flexible, particularly in distal sections thereof, to pass through the tortuous regions. Difficulties in endovascular positioning, however, make it desirable to impart high tensile and column strength over at least the proximal portion of the catheter. Additionally, the blood vessels of the brain are relatively fragile, so it is desirable that the catheter have a soft, non-traurmatic exterior to prevent injury. U.S. Pat. Nos. 4,464,176 to Wijayrathna and 4,739,768 to Engelson describe such catheters consisting of an inner layer and an outer layer, where the inner layer terminates proximally of the outer layer to form a relatively more flexible distal catheter section in the range of 4.0 cm in length. A large number of designs of neurological catheters for introduction over a guidewire or that are intended to be flow directed have been described in the prior art wherein the catheter body is formed of two or three or more sections of increasing flexibility distally and terminating in a distal soft tip. Such flow directed catheters are described, for example, in U.S. Pat. No. 5,336,205 to Zenzon et al. Commonly assigned U.S. Pat. No. 5,676,659 to McGurk, discloses a microcatheter body having a continuous outer layer overlying a wire braid formed over a tubular inner liner or layer to form a reinforced proximal catheter section, a more flexible intermediate section formed of the inner and outer layer without the wire braid, and terminating in a distal soft tip or distal catheter section formed only of the outer layer. It is also suggested that the pitch or characteristics of the wire braid can be varied through the proximal catheter section to increase the flexibility of the proximal catheter section distally. The formation of these catheter sections on a discrete catheter body involves use of discrete outer tubes placed over the inner jacket, heat shrink tubes placed over the outer tubes, baking the assembly in an oven, and removing the heat shrink tubes.

Finally, infusion wires have been developed that combine the functions of a guidewire with the capability of delivering an infusate while the guidewire is positioned in a blood vessel to allow introduction of other catheters or medical devices over the infusion wire. Such infusion wires are typically formed of wire reinforced proximal catheter sections that are relatively stiff to aid in pushability and torqueability and more flexible distal catheter sections that can be curved to make turns in tortuous vasculature. One such open ended infusion wire is disclosed in U.S. Pat. No. 5,178.158 to de Toledo.

As can be seen from the prior art, many common techniques, materials and constructions are employed in the fabrication of medical catheters and infusion wires of a wide range of sizes for the various medical diagnostic and therapeutic procedures. In almost all cases, medical catheter bodies need to have relatively stiff proximal catheter sections to aid in advancing the catheter distal tip to the site of interest and a relatively soft or otherwise atraumatic distal tip to avoid damage to the vasculature, tract, duct, or cavity wall it is advanced through or to. Most such catheters for vascular use now employ one or more intermediate catheter sections of intermediate flexibility or some manner of increasing flexibility of the catheter body distally so that the distal end catheter section can be advanced through a tortuous pathway. The fabrication of these catheters can be complicated and expensive. There remains a need for a fabrication technique that simplifies fabrication steps and reduces cost while retaining desirable characteristics of the catheter body.

SUMMARY OF THE INVENTION

It is therefore an object of the present invention to simplify and reduce the cost of fabrication of medical catheters of the type described above.

The present invention provides improved fabrication methods for catheters of the type having an elongated catheter body and catheter hub at the proximal catheter body end with at least one catheter lumen extending through the catheter hub and body and to a distal catheter body end thereof, and catheters formed thereby. The catheter body is formed of at least a proximal catheter section coupled at its proximal end to the catheter hub and a distal catheter section coupled at a junction with the distal end of the proximal catheter section and terminating at a distal end of the distal catheter sections. One or more intermediate catheter sections are optionally formed between the proximal and distal catheter section. The distal catheter section can comprise a relatively short distal soft tip or a separately formed distal soft tip can be attached to the distal end of the distal catheter section.

Catheters constructed in accordance with the principles of the present invention comprise a catheter body having a proximal catheter body end and a distal catheter body end and formed of a proximal section and at least one distal section that have differing flexibilities, wherein the catheter body is formed in a process comprising the steps of: (1) forming a continuous tubular inner jacket; (2) forming short initial layer segments of an initial segment thickness along the length of the inner jacket from a material of first durometer hardness, whereby each initial layer segment is separated apart by a separation distance; (3) forming a final layer of a material of second durometer hardness in a layer thickness over the tubular inner jacket along the separation distances and over and/or against the proximal and distal initial layer ends of the initial layer segments to form a continuous catheter body tubing; (4) severing the continuous catheter body tubing into catheter body lengths including a proximal catheter section formed of the material of second durometer hardness and a distal catheter section formed of the material of first hardness; and (5) completing the catheter fabrication at the proximal catheter body end and the distal catheter body end.

In step (3), the thickness of the final layer can be less than, equal to or greater than the thickness of the initial layer segments. In step (5) or in an intermediate step between steps (3) and step (4), centerless grinding can be employed to render the catheter body diameter uniform and/or to reduce the final outer diameter of the catheter body or catheter body tubing, respectively, to remove any final layer material overlying the proximal catheter section of the catheter body.

In a first variation of the method of the present invention, in a further step between steps (2) and (3), an intermediate segment layer of a material having a further durometer hardness is formed over the tubular inner jacket in an intermediate segment length and an intermediate segment thickness in proximity to each initial layer segment. The final layer forming step (3) further comprises forming the final layer over the tubular inner jacket along the separation distances and over the initial and intermediate segment layers to form the continuous catheter body tubing. The severing step (4) further comprises severing the continuous catheter body tubing into catheter body lengths including a proximal catheter section formed of the material of second hardness an intermediate catheter section formed of the material of intermediate hardness, and a distal catheter section formed of the material of first hardness over the inner jacket.

More particularly, the first material preferably is a softer durometer material than the second material (and the intermediate material, if present) whereby the resulting distal catheter section is more flexible than the proximal catheter section, although it is possible to selectively employ a first material that is harder than the second material to provide a less flexible distal section.

The first material (and the intermediate material, if present) is preferably molded over the continuous catheter body tubing in a cylinder, although it may be molded in a linear band, e.g., as a half cylinder section. The second material is preferably molded as a cylinder over the tubular inner jacket along the separation distances and over the first layer segments (and intermediate segment layers, if present) to form a continuous, cylindrical, catheter body tubing. The first and any intermediate segment layers are preferably molded or extruded to the inner jacket with tapered end edges so that they mutually engage one another (if both are present) and the second layer in a tapered edge manner.

The tubular inner jacket can be of any construction but is preferably formed in the first step of an inner tubular layer or liner composed of a lubricious material continually formed over a wire or plastic mandrel in a coating or continuous extrusion process. The use of such materials provides a very smooth lumen surface after the mandrel is removed for introducing devices and high velocity fluids through the lumen. The tubular inner jacket is preferably reinforced by any of the reinforcement processes, including use of multiple wall layers, including preferably the use of a reinforcement layer disposed over the outer surface of the tubular inner liner. Thus, the first step further preferably comprises continuously forming a reinforcement layer over the outer surface of the tubular inner liner. The reinforcement layer preferably comprises a braided reinforcement layer composed of a filament braid, preferably employing stainless steel or polymeric filaments, which is tightly braided over the outer surface of the tubular inner liner. The other layer segments and the final layer are then formed over the braided reinforcement layer. The flexibility of the catheter body is controlled by selecting the relative lengths and mechanical characteristics of each of these components.

The invention can be practiced using further tubular inner jackets. For example, the reinforcement of the tubular inner jacket, e.g., the reinforcement layer, can be either not formed or can be selectively removed in the first step (1) to expose inner liner surface lengths along the length of the inner tubular jacket are separated apart by the separation distance. Then, the initial material layer is formed over the exposed length. If a transition or intermediate catheter section is to be formed, the intermediate hardness material layer can be formed over the reinforcement adjacent to the initial material layer as described above. Alternatively, the exposed inner liner surface can be extended to an exposed length, and the initial material and the intermediate material can be formed in adjacent layer segments over that entire length. Again, however, the intermediate hardness material layer may be alternatively formed over the exposed length.

Larger diameter angiography and guide catheters formed in accordance with the present invention can have a separately formed distal soft tip segment attached to the distal catheter body end in the final fabrication step as a distal soft tip in any of the manners described above in the prior art. In such cases, a single transition from the tubular inner liner lumen to the contiguous lumen defined by the distal soft tip exists. However, the single transition can be eliminated in catheters formed in accordance with the methods of the present invention wherein the second material and the inner jacket material are suitably selected to be soft and flexible.

Employing these techniques in the different sections of the catheter body, flexibility, tensile strength, column strength, and hoop strength may be varied as desired by selectively controlling the mechanical characteristics of one or more of the formed catheter sections. Moreover, the fabrication process of forming the segment layers over prescribed segment lengths of the tubular inner jacket and then forming the continuous catheter body tubing enhances the uniformity of the characteristics of the catheter bodies cut from the continuous catheter body tubing. Costs of fabrication are also reduced.

In the exemplary embodiments, the major proximal section of the catheter body extending from its proximal end to the distal or intermediate catheter section is the least flexible, but has excellent torque transmission and hoop strength characteristics. The distal catheter section possesses the greatest flexibility with the minimum torqueability and hoop strength. The distal and any intermediate catheter section has or have greater flexibility while retaining adequate torqueability and hoop strength to permit guiding of the catheter by itself or over a guide wire and prevent kinking and collapse of the catheter lumen.

The methods of construction involve molding and extrusion techniques that result in a continuous catheter body tubing having the catheter sections formed thereon in repetitive patterns along the length thereof. Each junction of adjoining catheter sections is integrally formed and secure from fracture in use. Catheter bodies are cut from the continuous catheter body tubing, and the catheter fabrication is completed by trimming and finishing steps. The fabrication methods are therefore efficient and less costly and result in uniform product.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the invention will become apparent from the following detailed description of the preferred embodiments of the invention, in which:

FIGS. 10–14 are partial cross-section views of a catheter body distal portion in the stages of fabrication of the flow chart of FIG. 9;

FIGS. 17–21 are partial cross-section views of a catheter body distal portion in the stages of fabrication of the flow chart of FIG. 16;

FIG. 22 is a flow chart of a further simplified fabrication process for forming a catheter of the type depicted in FIG. 15;

DETAILED DESCRIPTION OF THE PREFERRED EMBODIMENTS OF THE INVENTION

Figure 1:
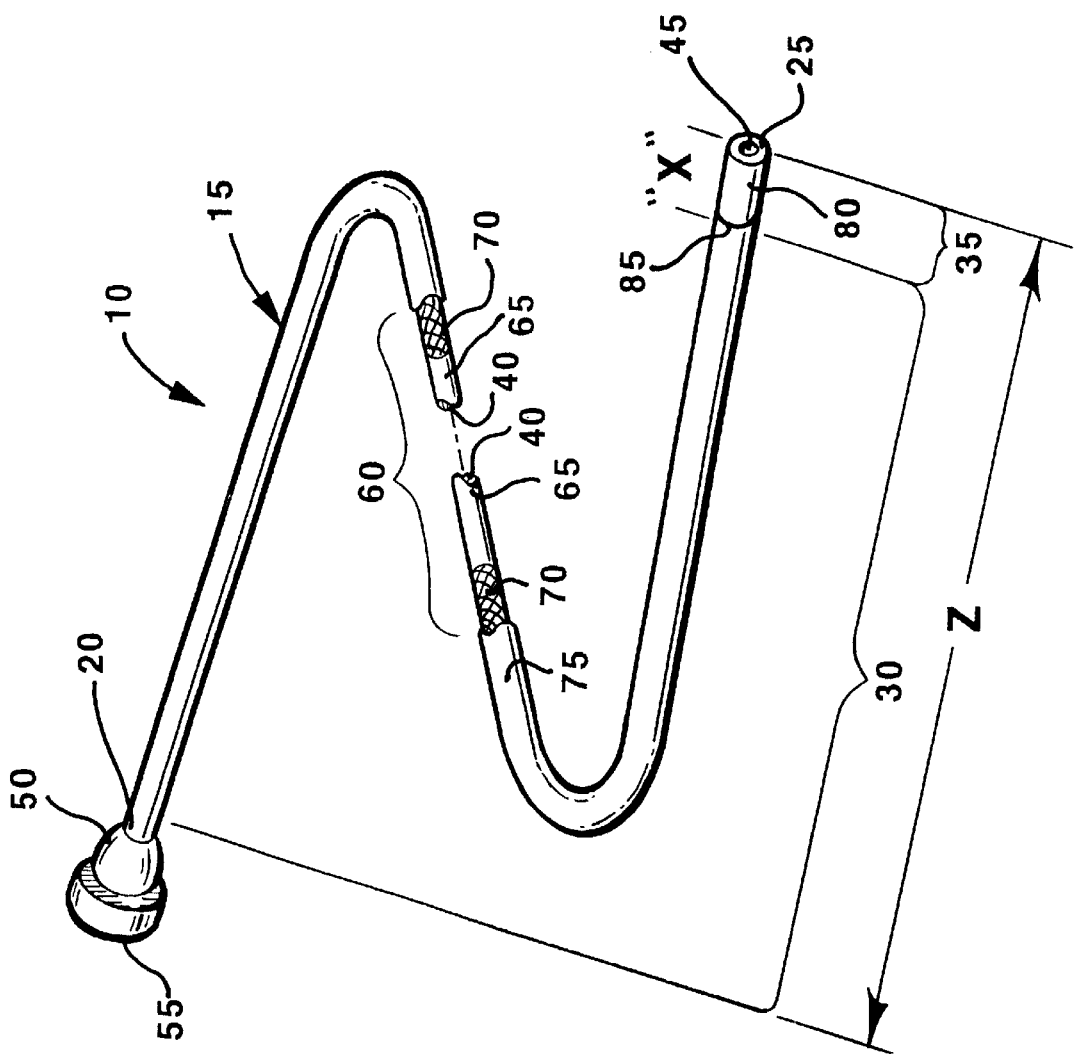
FIG. 1 is a schematic illustration of a typical catheter formed in accordance with the methods of fabrication of the present invention to have a proximal catheter section and a distal catheter section that can comprise a distal soft tip.

FIG. 1 illustrates a two section embodiment of a medical catheter 10 constructed in accordance with the principles of the present invention having a catheter body 15 extending between a proximal catheter body end 20 and a distal catheter body end 25 and formed of a proximal catheter section 30 and a distal catheter section 35 that have differing flexibilities. The flexibility of the catheter body 15 is controlled by selecting the relative lengths and mechanical characteristics of each of these components. A catheter lumen 40 extends through the length "Z" of the catheter body 15 from a catheter lumen distal end opening 45 to a proximal connector 50 and then extends proximally through connector 50 to a catheter lumen proximal end opening 55. The catheter lumen 45 is provided within an inner liner of a tubular inner jacket 60 described below and allows for the passage of a diagnostic or therapeutic fluid or other device through it and/or allows for the catheter body 15 to be advanced in an OTW manner over a guidewire or infusion wire previously advanced to a site of interest in a patient's body.

Proximal hub or connector 50 can be any standard medical interconnection device that provides for the introduction of a diagnostic or therapeutic fluid or other device through the catheter lumen 40 and out of the lumen distal end opening 45. The proximal connector 50 can be a luer fitting, for example, wherein the diagnostic or therapeutic fluid or other device is introduced through lumen proximal end opening 55 into the catheter lumen 40 in the illustrated case. Alternatively, the proximal connector 50 can optionally include one or more side port extensions for infusion or withdrawal of fluids through the catheter lumen 45. In such a case, a penetrable seal mechanism can be formed across the lumen proximal end opening to seal against a guidewire or infusion wire or other medical device advanced through it and into the catheter lumen 45 to inhibit backflow of blood or body fluids and any infused fluids.

The catheter body 15 is denoted as having an overall length "Z" and includes a proximal catheter shaft or section 30 of length approximately "Z"–"X" between the proximal catheter end 20 to the junction 85 and a distal catheter section 35 of length "X" extending between the junction 85 and the distal catheter body end 25. These length terms are employed in the fabrication process described below and are somewhat approximate due to overlapping and trimming variables as described below.

The proximal catheter section 30 and certain embodiments of the distal catheter section 35 of the catheter body 15 are formed of a tubular inner jacket 60 that is preferably reinforced by any of the reinforcement processes known in the catheter art. Such reinforced tubular inner jackets can be formed of multiple continuous wall layers e.g. polyamide tube or hypotube coated by a softer tubular layer or the like, or of a tubular inner liner 65 covered by a reinforcement layer 70 disposed over the outer surface of the tubular inner liner 65 as illustrated in FIG. 1. The tubular inner liner 65 is composed of a lubricious material, such as a fluorocarbon polymer, a polyamide (e.g., Nylon), polyether block amides (PEBA), a polyolefin, a polyimide, or the like. In one preferred embodiment, the inner liner 65 is extruded of Shore 70D PEBAX® polyether block-polyamide. In another preferred embodiment, the tubular inner liner is formed of polytetrafluoroethylene (PTFE). The inner liner is continually formed over a wire or plastic mandrel in a coating or continuous extrusion process. The use of such materials provides a very smooth catheter lumen surface after the mandrel is removed for introducing devices and high velocity fluids through the catheter lumen. It would also be possible to form the inner liner 65 as a laminate structure comprising a non-lubricious outer layer and an inner lumen surrounding layer or coating of a more lubricious material.

The reinforcement layer 70 is preferably formed of metal wire filaments or plastic filaments braided together in the manner described above. The reinforcement layer preferably comprises a reinforcement layer composed of a filament braid, preferably employing stainless steel or polymeric filaments, which is tightly braided over the outer surface of the tubular inner liner. Preferably, rectangular wire filaments of stainless steel, a shape memory alloy (e.g., Nitinol), polymeric fibers, or the like, are used. The other layer segments and the final layer are then formed over the reinforcement layer or over exposed tubular inner liner surface segments as described below.

In one embodiment of the invention, the catheter body is formed with the reinforcement, e.g., the reinforcement layer 70, extending all the way to the catheter body distal tip 45 or only to the junction 85. The braid structure is preferably square cut or otherwise smoothed in the fabrication process, so that it terminates cleanly at the desired termination location and is free from protrusions, burrs, and other discontinuities which could extend out of the catheter body and subject the patient to injury. In one form of a guide or angiographic catheter formed in accordance with a method of the invention, the reinforcement layer 70 extends to the catheter body distal tip 45 and a further distal soft tip is butt or lap joined thereto in a manner well known in the art. In a further form of such a large diameter catheter, the reinforcement layer 70 terminates at the junction 85, and the distal catheter section 35, trimmed to a suitable length "X", constitutes an integrally formed distal soft tip.

In the proximal catheter section 30, the illustrated reinforcement layer 70 of the tubular inner jacket 60 is covered by a proximal outer layer 75. Similarly, in the distal catheter section 35, either the reinforcement layer 70 of the tubular inner jacket 60 or the inner liner 65 of the tubular inner jacket 60 is covered by a distal outer layer 80, depending on whether the reinforcement layer 70 is present or not. The distal outer layer 80 is formed of a material of first hardness, and the proximal outer layer 75 is formed preferably of a material of second hardness. The first material preferably is a softer material than the second material, whereby the resulting distal catheter section 35 is more flexible than the proximal catheter section 30, although it is possible to selectively employ a first material that is harder than the second material to reverse the flexibility change. The catheter 10 of FIG. 1 thus preferably has a catheter lumen 40 with a uniform lumen diameter through its length and catheter outer layers 75 and 80 that have a common, uniform outer diameter.

The catheter body 15 of an angiography catheter can be "straight" as depicted in FIG. 1 or can be pre-curved into an Amplatz-type shape, a Judkins-type left shape or a pigtail shape, for example, wherein the distal catheter section is curved to the shape. The methods of the present invention can be employed to reinforce the curvature by employing a soft durometer material along the inside of the curve and a hard durometer material along the outside of the curve.

Figure 2:
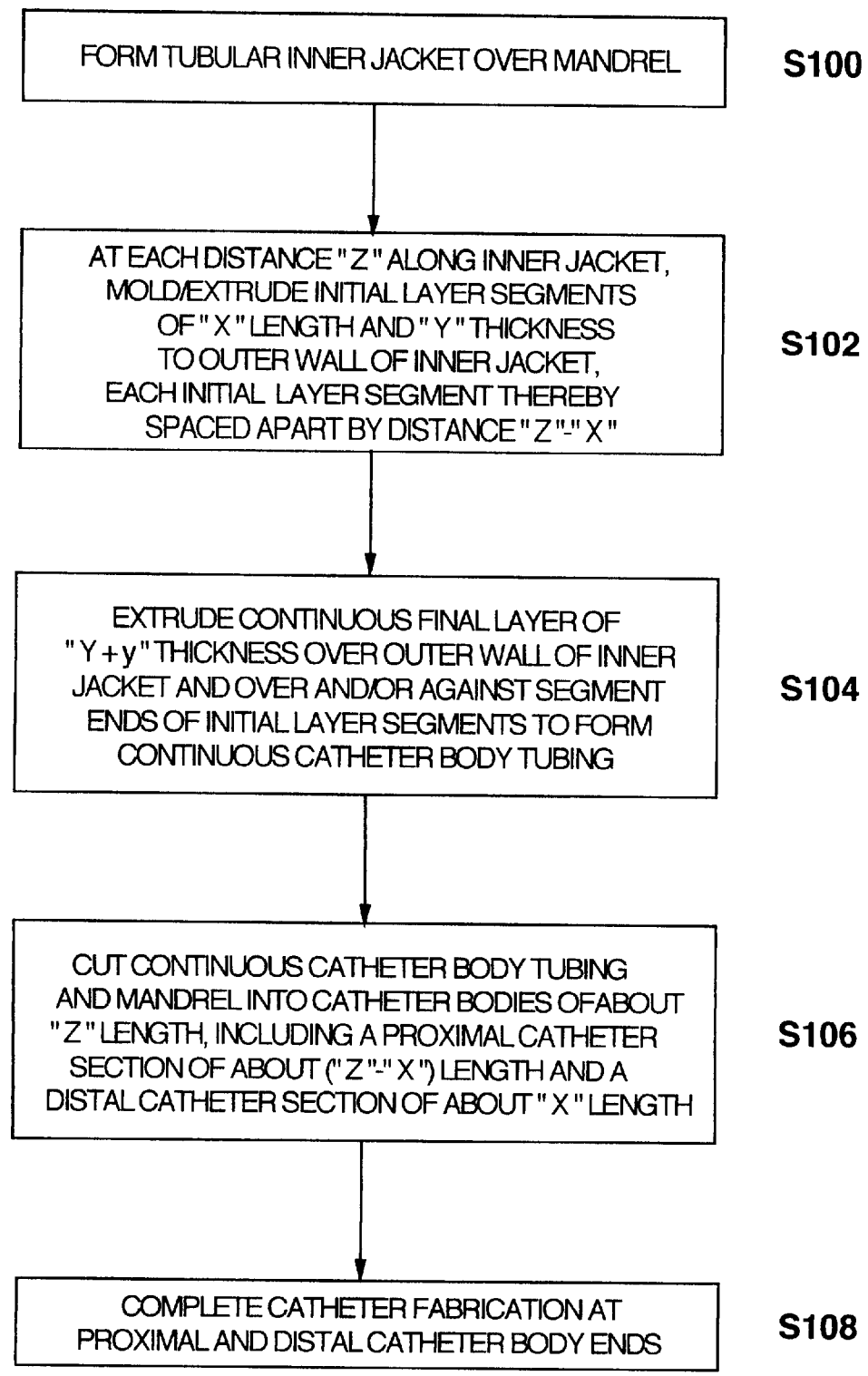
FIG. 2 is a flow chart of a simplified fabrication process for forming a catheter of the type depicted in FIG. 1.
Figure 3:
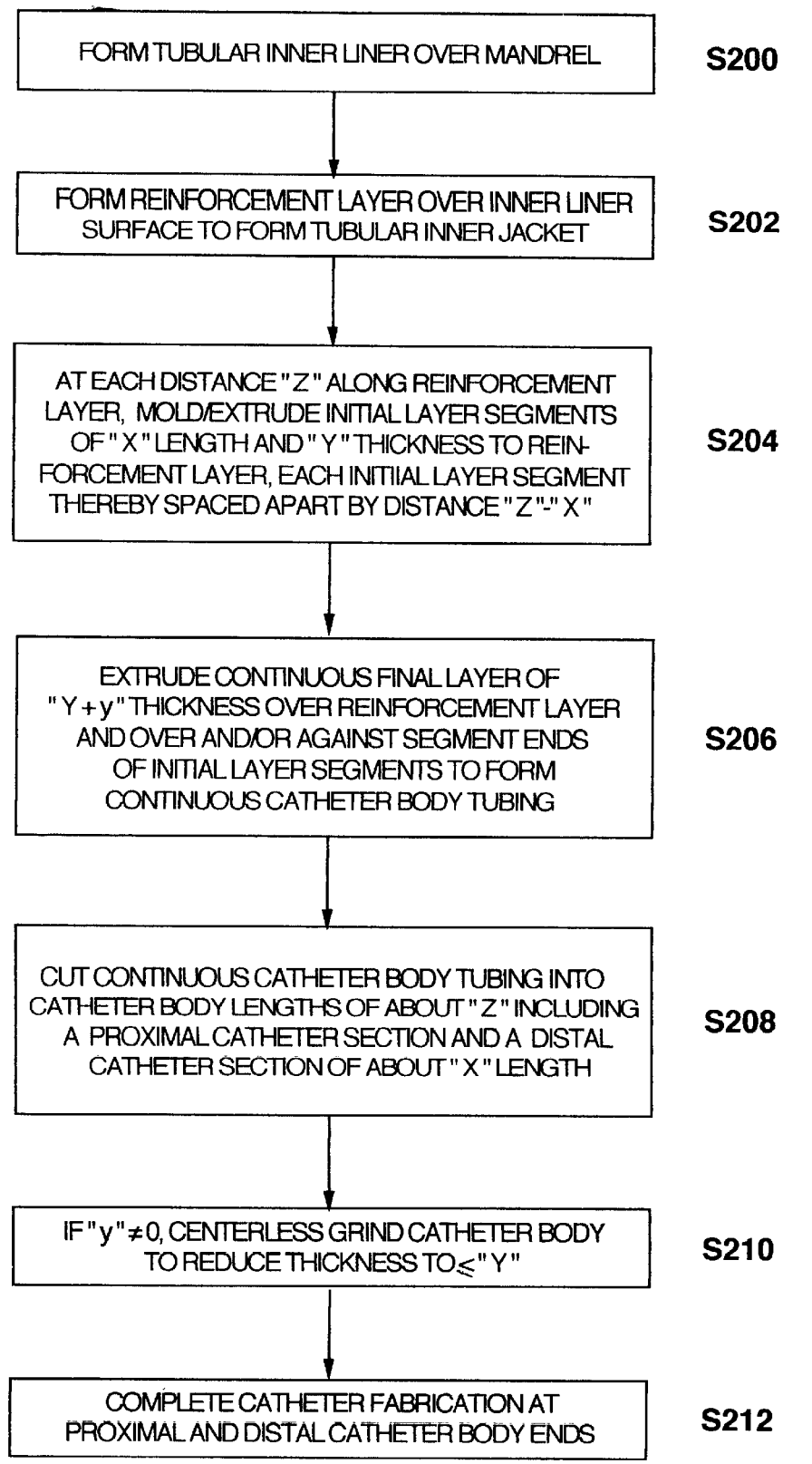
FIG. 3 is a flow chart of a further simplified fabrication process for forming a catheter of the type depicted in FIG. 1.
Figure 7:
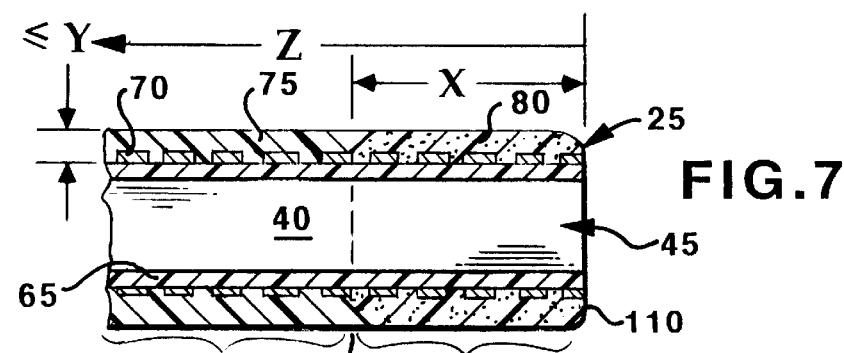
Figure 8:
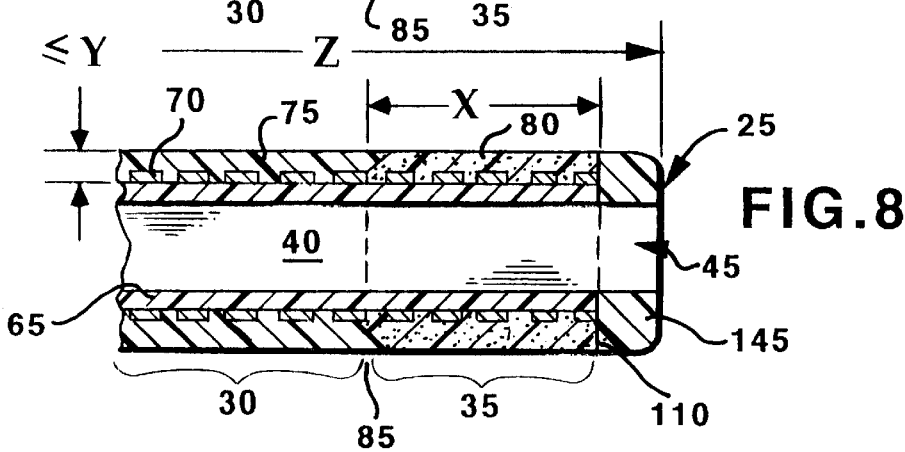
FIG. 8 is a partial cross-section view of a distal catheter body end formed in accordance with the fabrication steps of FIGS. 1 and 2 and having a distal soft tip attached thereto in the final fabrication step.
Figure 9:
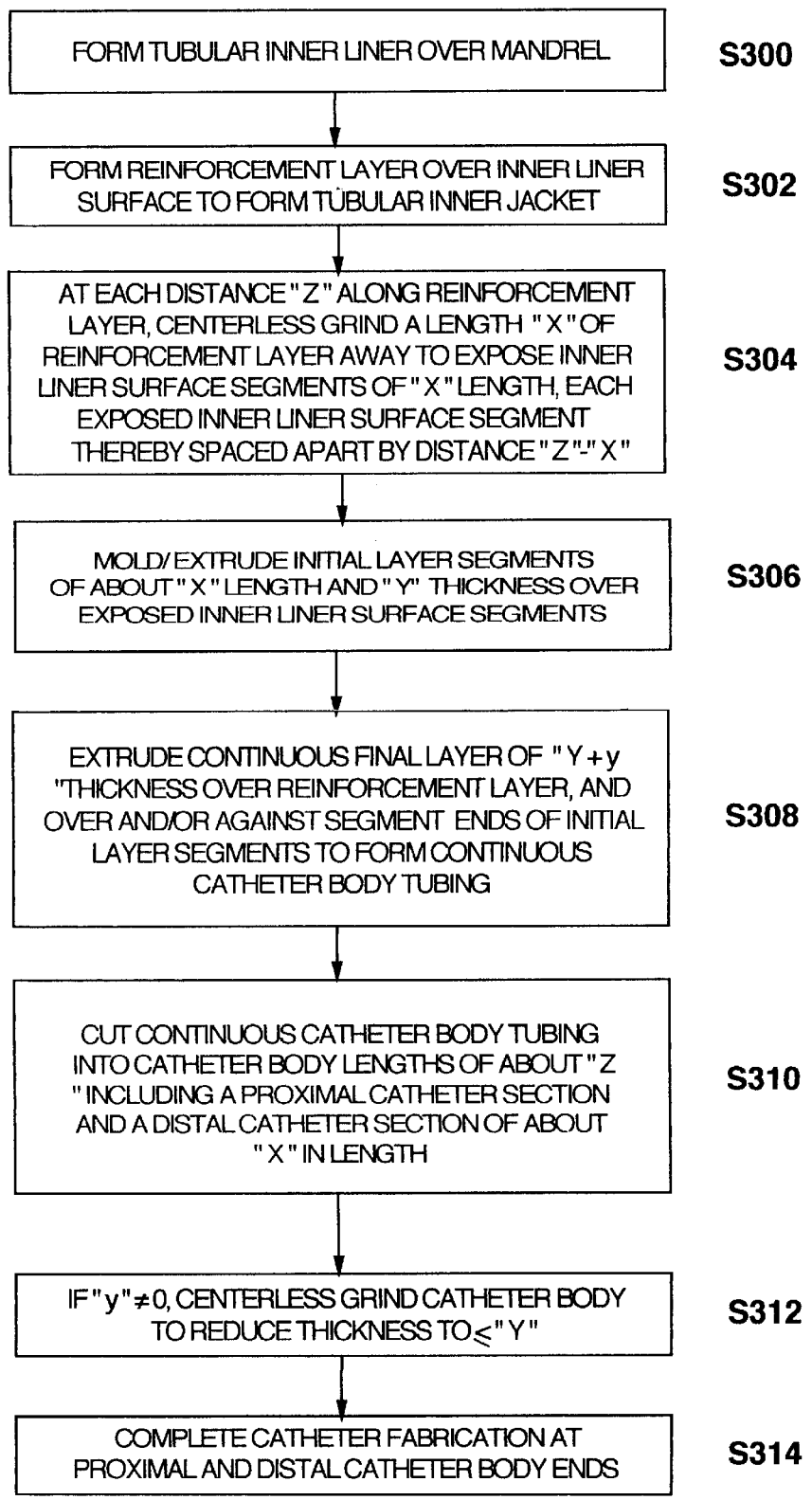
FIG. 9 is a flow chart of a still further simplified fabrication process for forming a catheter of the type depicted in FIG. 1.

The catheter of FIG. 1 is formed in accordance with the methods of the present invention illustrated in FIGS. 2–14. FIG. 2 sets forth the steps of the invention in a more general manner applicable to any form of tubular inner jacket, and without certain finishing steps, and FIG. 3 sets forth the preferred steps of forming the catheter of FIG. 1. FIGS. 4–7 illustrate these steps in greater detail, and FIG. 8 illustrates an optional addition to the final fabrication step. FIG. 9 sets forth a further method of forming the catheter of FIG. 1, and FIGS. 10–14 illustrate those steps.

In FIG. 1, the catheter body 15 comprising the proximal catheter section 30 and the distal catheter section 35 is formed in a continuous process wherein the tubular inner jacket may take any of the forms known in the art and include continuous tubular reinforcement layers or spiral wound, circular or flattened, reinforcement layers of the typed disclosed in the above-referenced '158 patent to de Toledo, for example. A continuous tubular inner jacket of indeterminate length is formed in step S100, preferably over a continuous wire or plastic mandrel.

A plurality of initial layer segments having a length "X" and thickness "Y" are formed each distance "Z" along the length of the inner jacket from a material of first durometer hardness in step S102. For a wide range of catheters, "X" can be selected in a range between 0.2 cm and 20 cm, and "Z" can be selected in a range between 60 cm and 200 cm. For example, where "X"=10 cm and "Z"=100 cm, the separation between successive initial layer segments is "Z"–"X" or 90 cm.

The initial layer segment can be cylindrical extending all the way around the circumference of the inner jacket or it can be formed in stripes along one side of the inner jacket. In this case, the material of first durometer hardness is preferably a relatively "soft" durometer material that is injection molded or extruded over the inner jacket so that each initial layer segment is a relatively flexible layer segment of thickness "Y". The materials of first durometer hardness can be selected from the group consisting of polyamide polyether block amides, (PEBAX® or VESTAMID®), polyurethane, polyethylene, silicone rubber, polyimides, nylon, fluorinated hydrocarbon polymers and the like in a hardness range from 30 A to 75 D, and the materials of second durometer hardness can be selected from the same group in a greater hardness than the materials of first durometer hardness.

However, in one particular example related to a shaped distal catheter section, materials of differing durometer hardness can be formed in lines on opposite sides of the inner jacket over a length "X". When a shape is to be formed, in the distal catheter section in the final step of fabrication, e.g. the Amplatz-type shape, a Judkins-type left shape or a pigtail shape, for example, a soft durometer material can be molded or extruded in a line along the inside of the curve to be formed and a hard durometer material can be molded or extruded along the outside of the curve. The shape in the distal catheter section is then formed in step S108 by inserting a shaped mandrel through the catheter lumen and then heating and cooling it. The resulting curved shape is more flexible on the interior side of the curve than on the outer side of the curve, tending to reinforce the maintenance of the shaped distal catheter section.

Radiopaque materials can be incorporated into the material of first hardness as described, for example, in the above-referenced '447 patent to Flynn and '270 patent to Parker.

Then, in step S104, a continuous catheter body tubing is formed from which catheter bodies can be cut to specified length "Z". A final layer of a material of second hardness is continuously formed over the tubular inner jacket along the separation distances "Z"–"X" between and preferably extending over the initial layer segments of length "X" to form a continuous catheter body tubing outer layer formed by one or the other or both of the materials of first and second hardness. The final layer is preferably formed by extrusion of a continuous layer with a thickness "Y"+"y", which is preferably equal to or greater than "Y". In this way, a continuous outer layer of "Y"+"y" thickness is formed overlying the outer wall of the inner jacket between the initial layer segments and extending between or preferably overlying the initial layer segments. The final layer material has a second durometer hardness that is preferably harder than the initial material, so that a relatively stiff continuous outer layer of the continuous catheter body tubing is formed in this step.

In step S106, the continuous catheter body tubing and the mandrel are cut into catheter bodies of about "Z" length, including a proximal catheter section of about "Z"–"X" length formed of the material of second hardness and a distal catheter section of about "X" length. The proximal catheter section is formed of the layer of the final material of second hardness and the tubular inner jacket, and the distal catheter section is formed of the layer of the initial material of first hardness and the tubular inner jacket and a layer of thickness "y" of the final material of second hardness, if "y">0. In this case, the material of second hardness is harder than the material of first hardness, and consequently, the distal catheter body section is more flexible than the proximal catheter body section.

In step S108, fabrication of the catheter is completed by removing the mandrel from the catheter lumen, trimming and dressing the catheter body and the distal catheter body end and attaching the proximal connector 50 to form the catheter 10 as it appears in FIG. 1. The junction 85 constitutes the area of intimate contact of the initial layer segment material with the final layer material. These materials are selected to be compatible and capable of adhering together in the extrusion of the final layer over the inner jacket and against or over the initial layer segment.

A preferred embodiment of the method is illustrated further in FIGS. 3–7 wherein the particular tubular inner jacket 60 illustrated in FIG. 1 is formed in steps S200 and S202 over a wire or plastic mandrel 90 employing fabrication techniques described, for example, in the above-referenced '659 patent to McGurk or the '416 patent to Macauley et al. However, in those cases, each catheter body is separately formed by placing or forming a length of the tubular inner liner over a mandrel and then forming the reinforcement layer over that length. In the fabrication methods of the present invention, the mandrel 90 is of an indeterminate length well exceeding the length of the catheter bodies to be formed.

The tubular inner liner 65 is first formed by deposition or extrusion over the mandrel 90 of the aforementioned PTFE material, for example, and the reinforcement layer 70 is formed over its exterior surface to provide a continuous tubular inner jacket 60 in a manner similar to that disclosed in the above-referenced '226 patent to Markling and the '742 patent to Stevens, prior to the removal of sections of the reinforcement layer. While the reinforcement layer 70 is depicted in FIGS. 4–7 as formed of flattened metal or plastic filaments, it will be understood that it can be formed of round metal or plastic filaments as disclosed, for example, in the above-referenced '270 patent to Parker, or in any of the forms described above with respect to FIG. 2.

Figure 4:
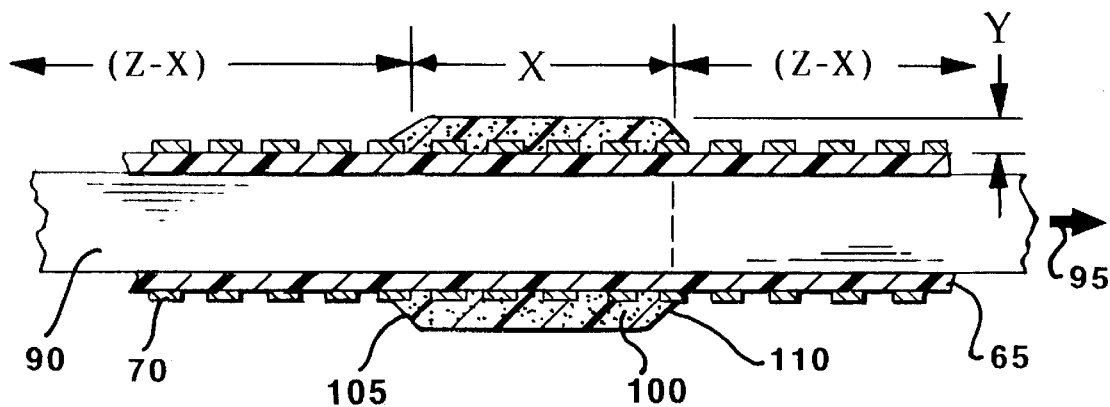
FIGS. 4–7 are partial cross-section views of a catheter body distal portion in the stages of fabrication of the flow charts of FIGS. 2 and 3.

FIG. 4 illustrates a length of the tubular inner jacket 60, comprising the reinforcement layer 70 overlying the tubular inner liner 65, that is formed over mandrel 90 in steps S200 and S202. FIG. 4 also illustrates the advancement of the tubular inner jacket 60 and mandrel 90 distance "Z" in the direction of the arrow 95 to locate a section of length "X" thereof in a molding or extrusion cavity (not shown). At this point in step S204, the cylindrical initial layer segment 100 of length "X" is formed over the section of length "X" as shown in FIG. 4. After each such initial layer segment 100 is formed, the tubular inner jacket 60 over the mandrel 90 is advanced in the direction of advancement 95 a distance "Z", and the process is repeated, resulting in a plurality of such initial layer segments 100 formed over the tubular inner jacket 60 and each separated from its neighbor by a separation distance "Z"–"X", The initial layer segment proximal end 105 and the initial layer segment distal end 110 are preferably tapered in the molding or extrusion process to provide for an overlapping of the: initial layer segment 100 with the final layer (or an intermediate segment layer) as described below.

Figure 5:
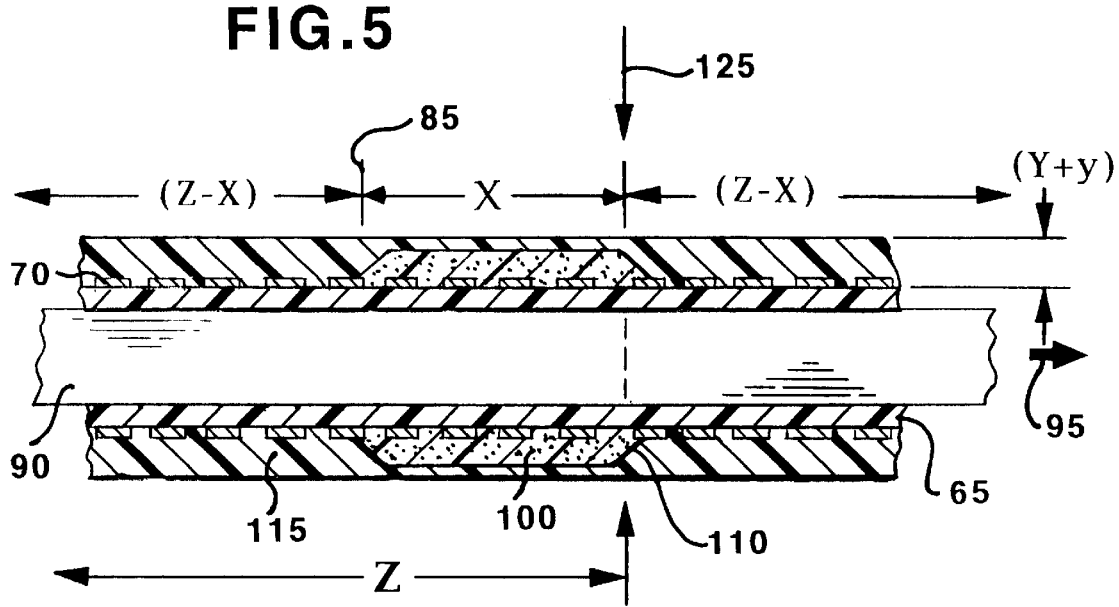

FIG. 5 depicts the continuous formation of a final layer 115 of a material of second hardness, the final layer formed with "Y"+"y" thickness over the tubular inner jacket 60 along the separation distances "Z"–"X" and over the initial layer segments 100 (if "y">0) to form a continuous catheter body tubing 120 in accordance with step S206. The continuous extrusion process results in an overlapping, ring shaped, layer of the material of the final layer 115 extending over the tapered initial layer segment proximal end 105 and initial layer segment distal end 110. Strong adhesion of the melted material of second hardness with the solid material of first hardness used in the initial layer sigment is accomplished by selecting compatible materials that have close melting temperatures, whereby at least a surface layer of the material of first hardness melts upon contact with the molten material of second hardness and subsequently cools and solidifies forming an integral bond.

Thus, a continuous catheter body tubing of indeterminate length is formed in this manner. Catheter bodies 15 are then or later cut from the continuous catheter body tubing and formed into a catheter 10. In step S208, the continuous catheter body tubing is cut into catheter body lengths of about "Z" at the catheter body cut lines 125 shown in FIG. 5. At this point, if "y"=0, then the final step S212 can be followed to complete the fabrication of the catheter as described above with respect to step S108 of FIG. 2. If "y" is not equal to 0, then it is desirable to follow step S210 of FIG. 3 to make the outer diameters of the proximal catheter section and the distal catheter section the same. Regardless of the value of "y", following step S210 is preferred, and it is illustrated in FIG. 6 for the case where "y">0.

Figure 6:
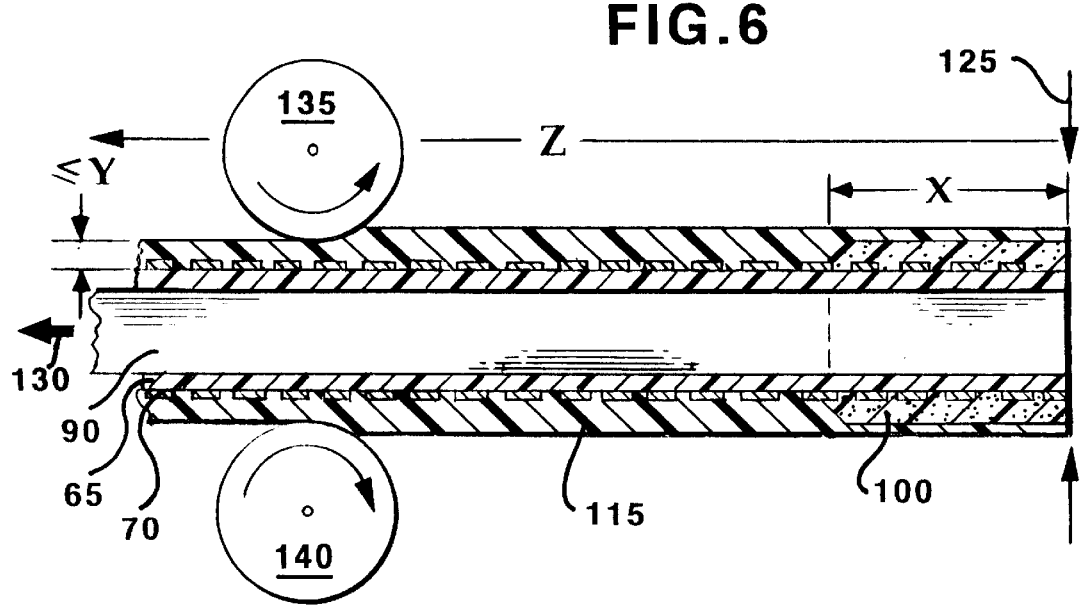

In this case, the catheter body length supported by the mandrel 90 is advanced in a centerless grinding advance direction 130 through a centerless grinding machine illustrated schematically by the grinding wheels 135 and 140 to reduce the thickness of the initial layer segment 100 and the final layer 115 to ≦"Y" as shown in FIG. 6. The centerless grinding process exposes the outer surface of the initial layer segment 100. Although this step S210 is depicted and described as occurring after the continuous catheter body tubing is cut into catheter body lengths, it could also be conducted before the cuts are made along catheter body cut lines 125.

In step S212, the cut section of the mandrel 90 is removed, and final fabrication of the catheter 10 is completed. The catheter distal tip 25 is shaped and any protrusions, burrs, discontinuities, or the like, which may result from the termination of the braid at the cut lines 125 are trimmed. As shown in FIG. 7, the distal outer layer 80 is formed by the initial layer segment 100, and the proximal outer layer 75 is formed by the final layer 115. The resulting catheter 10 thus has proximal and distal catheter sections 30 and 35 of differing flexibility, and in the typical case, the distal catheter section 35 is more flexible than the proximal catheter section 30 by virtue of the selection of the materials of the initial layer segment 100 and the final layer 115. It will be understood that the length "X" is not necessarily to scale and can be substantially longer or shorter than illustrated depending on the intended use and characteristics of the catheter body 15

FIG. 8 is a partial cross-section view of a distal catheter body end formed in accordance with the fabrication steps of FIGS. 1 and 2 and having a discrete distal soft tip 45 attached thereto in the final fabrication step S212. The discrete distal soft tip 145 can also be formed at the distal catheter body end 25 of the other embodiments of the invention described hereafter. The distal soft tip 145 can be formed with radiopaque material encased therein and can be shaped and attached to form the distal catheter body end 25 in a manner disclosed in the above-referenced '910 patent to Lunn or the '149 patent to Brin et al. or in the above-referenced copending '241 patent application.

FIG. 9 is a flow chart of a still further simplified fabrication process for forming a catheter 10 of the type depicted in FIG. 1, wherein the reinforcement layer 70 is removed along the lengths "X" where the initial segment layers 100 are to be formed. FIGS. 10–14 are partial cross-section views of a catheter body distal portion in the stages of fabrication of the flow chart of FIG. 9. In FIG. 9, steps S300 and S302 correspond to steps S200 and S202 of FIG. 3 to form the tubular inner jacket 60. In this alternative method for forming a two section catheter body 15, the reinforcement of the tubular inner jacket 60, e.g., the reinforcement layer 70, can be either not formed or can be selectively removed, exposing a length "X" of the tubular inner liner 65 in step S304. In a continuous removal process also illustrated in FIG. 10, the lengths "X" of exposed inner liner surface 165 along the length of the inner tubular jacket 60 are removed by a centerless grinding machine schematically illustrated by grinding wheels 155 and 160. Each exposed inner liner surface 165 of length "X" is separated from one another by the distance "Z"–"X" along the continuous tubular inner jacket 60. The centerless grinding methods disclosed in the above referenced '226 patent to Markling and the '742 patent to Stevens can be employed in step S304.

In step S306, illustrated in FIG. 11, the initial layer segments 100 of length "X" are formed over the exposed inner liner surface segments 165, in substantially the same manner as step S204 and FIG. 4. In step S308, illustrated in FIG. 12, the continuous final layer 115 of a material of second hardness and in a thickness "Y"+"y" is extruded along the separation distances "Z"–"X" and over the initial layer segments 100 (if "y">0). A continuous catheter body tubing is formed thereby in substantially the same manner as step S206 and FIG. 5 as described above.

Again, after the continuous catheter body tubing is formed in this manner, it is cut into catheter body lengths of about "Z" in accordance with step S310 at the catheter body cut lines similar to lines 125 shown in FIG. 5. At this point, if "y"=0, then the final step S314 can be followed to complete the fabrication of the catheter as described above with respect to step S108 of FIG. 2. If "y" is not equal to 0, then it is desirable to follow step S312 of FIG. 9 to make the outer diameters of the proximal catheter section and the distal catheter section the same. Regardless of the value of "y", following step S312 is preferred, and it is illustrated in FIG. 13 for the case where "y">0.

Figure 13:
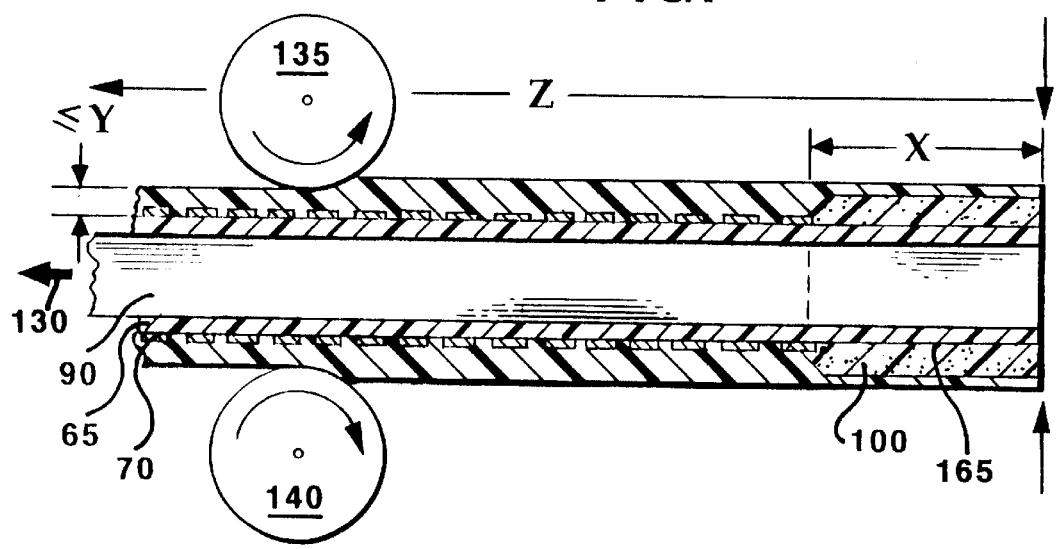

Again, the catheter body length supported by the mandrel 90 is advanced in a centerless grinding advance direction 130 through a centerless grinding machine illustrated schematically by the grinding wheels 135 and 140 to reduce the thickness of the initial layer segment 100 and the final layer 115 to ≦"Y" as shown in FIG. 13. The centerless grinding process exposes the outer surface of the initial layer segment 100.

Note that this step S312 is depicted and described as occurring after the continuous catheter body tubing is cut into catheter body lengths of about "Z" in step S310. However, step S312 could alternatively be conducted before the cuts are made along catheter body cut lines 125, so that the continuous catheter body tubing 120 is formed with the thickness of the initial layer segment 100 and the final layer 115 reduced to ≦"Y".

Figure 14:
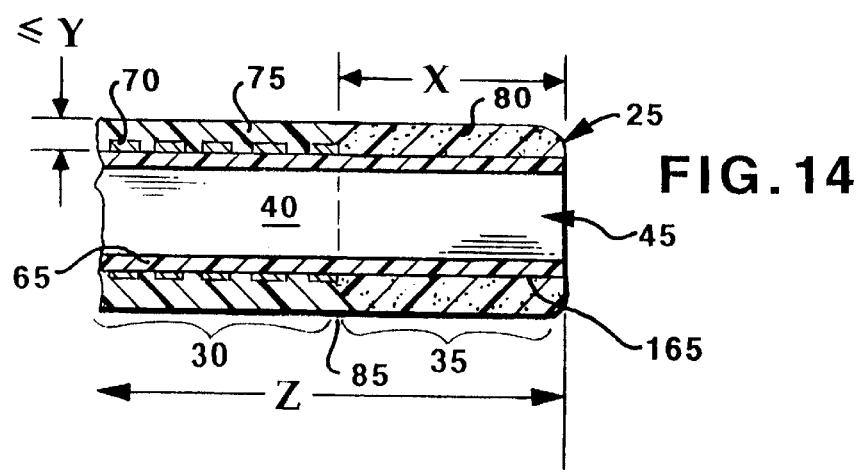

In step S314, the cut section of the mandrel 90 is removed from catheter lumen, and final fabrication of the catheter 10 is completed. The catheter distal tip 25 shown in FIG. 14 is shaped as described above with reference to FIG. 7. As shown in FIG. 14, the distal outer layer 80 is formed by the initial layer segment 100 overlying the exposed inner liner surface segment 165, and the proximal outer layer 75 is formed by the final layer 115 overlying the reinforcement layer 70. The resulting catheter 10 thus has proximal and distal catheter sections 30 and 35 of differing flexibility, and in the typical case, the distal catheter section 35 is more flexible than the proximal catheter section 30 by virtue of the selection of the materials of the initial layer segment 100 and the final layer 115 as well as the removal of the reinforcement layer 70 It will be understood that the length "X" is not necessarily to scale and can be substantially longer or shorter than illustrated depending on the intended.use and characteristics of the catheter body 15. The discrete distal soft tip 145 of FIG. 8 can also be attached to form the distal catheter body end 25 as described above with respect to FIG. 8.

Figure 15:
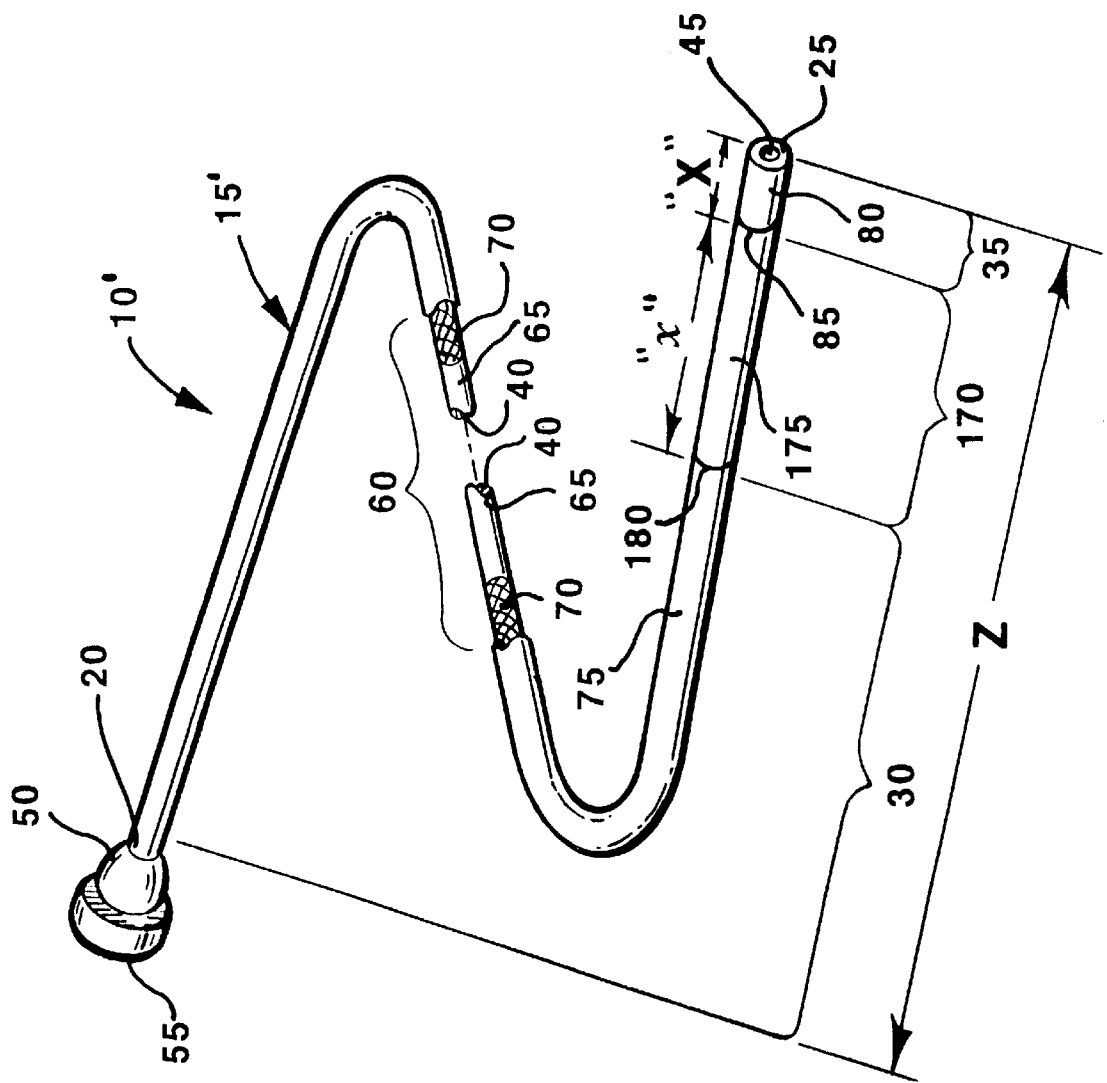
FIG. 15 is a schematic illustration of a typical catheter formed in accordance with the methods of fabrication of the present invention to have a proximal catheter section, an intermediate catheter section, and a distal catheter section that can comprise a distal soft tip.

These fabrication techniques result in a catheter body 15 of FIG. 1 that is formed of proximal and distal catheter sections optionally including a further distal soft tip. The principals of the present invention can be applied to the fabrication of medical catheters having one or more further intermediate catheter sections intermediate the proximal and distal catheter sections. FIG. 15 illustrates a three section embodiment of a medical catheter 10' constructed in accordance with the principles of the present invention also having a three section catheter body 15' extending between a proximal catheter body end 20 and a distal catheter body end 25 and formed of the proximal catheter section 30, the distal catheter section 35 and an intermediate catheter section 170, each having differing flexibilities. The flexibility of the catheter body 15' is controlled by selecting the relative lengths and mechanical characteristics of each of these components. A catheter lumen 40 extends through the length "Z" of the catheter body 15' from a catheter lumen distal end opening 45 to a proximal connector 50 and then extends proximally through connector 50 to a catheter lumen proximal end opening 55. The catheter lumen 40 is provided within an inner liner of a tubular inner jacket 60 preferably formed of a tubular inner liner 65 and a reinforcement layer 70 of any of the types described above. Although the catheter body 15' is shown in a straight configuration, it will be understood that it can be formed in a pre-curved configuration, where the curve extends through the distal catheter section 35 and/or the intermediate catheter section 170 and possibly a distal portion of the proximal catheter section 30.

The intermediate catheter section 170 is formed of an intermediate outer layer 175 and is of a length "x" that extends proximally from junction 85 to a proximal junction 180 with the proximal outer layer 75. In accordance with the preferred methods of fabrication described below, the intermediate catheter section 170 can be formed many different ways to provide a flexibility that differs from the flexibility of the proximal and distal catheter sections 30 and 35, respectively. In the typical case, the proximal catheter section 30 is formed to have sufficient column strength and hoop strength for advancement through the incision in the patient's skin and blood vessel and through the tortuous vasculature. The proximal catheter section side wall is formed to be relatively stiff to provide good torqueability and pushability, as these terms are understood in the art. The side wall of the intermediate catheter section 170 is formed to be more flexible than the proximal catheter section to provide for better maneuverability of the catheter through tortuous passageways. The side wall of the distal catheter section 35 is formed to have even greater flexibility to provide a soft distal tip and/or to allow OTW (over-the-wire) or flow advancement of the catheter body 15' through the tortuous passageways.

In the guide catheter context, the intermediate stiffness of the intermediate catheter section 170, which is typically pre-curved, provides backup support of the distal most segment that is introduced into a blood vessel. It inhibits the straightening of the curve and dislodgment of the distal segment from the previously accessed vessel when a further catheter is introduced through the catheter lumen.

Generally speaking, the catheter body 15' can be formed with a single initial layer segment and a final layer as described above formed over a tubular inner jacket 60, where the reinforcement layer 70 is removed to form exposed inner liner surface segments of length "X" or length "X+x" as further described below. In this approach, only two molding or extrusion steps are required, but the centerless grinding step is required to alter the flexibility of the underlying tubular inner jacket in these sections. A further intermediate segment layer can be formed of length "x" after or before formation of the initial layer segment of length "X", thereby requiring an additional molding or extrusion step. In this case, the centerless grinding step can still optionally be employed to selectively expose inner liner surface segments of length "X" or length "X+x".

Figure 16:
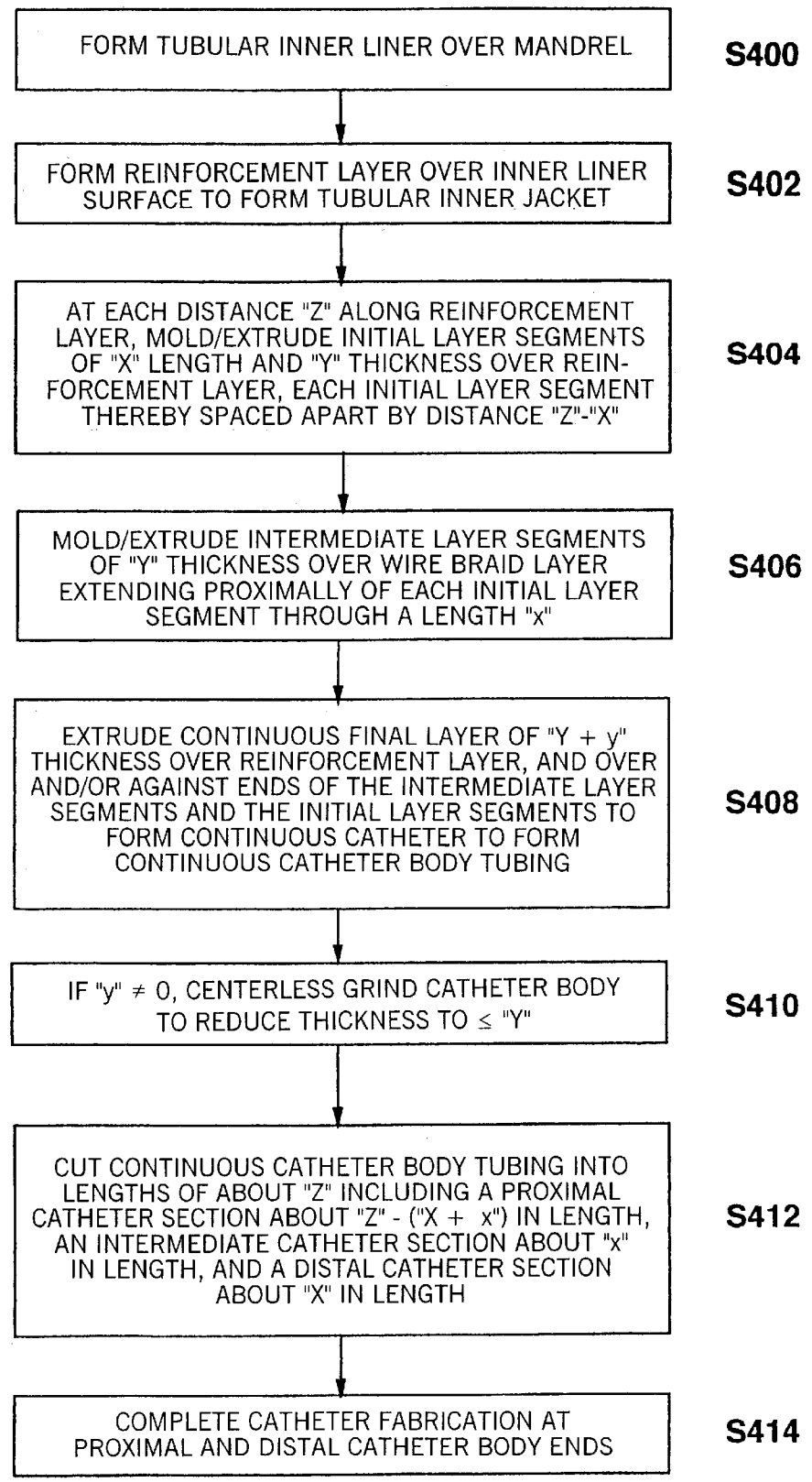
FIG. 16 is a flow chart of a simplified fabrication process for forming a catheter of the type depicted in FIG. 15.
Figure 17:
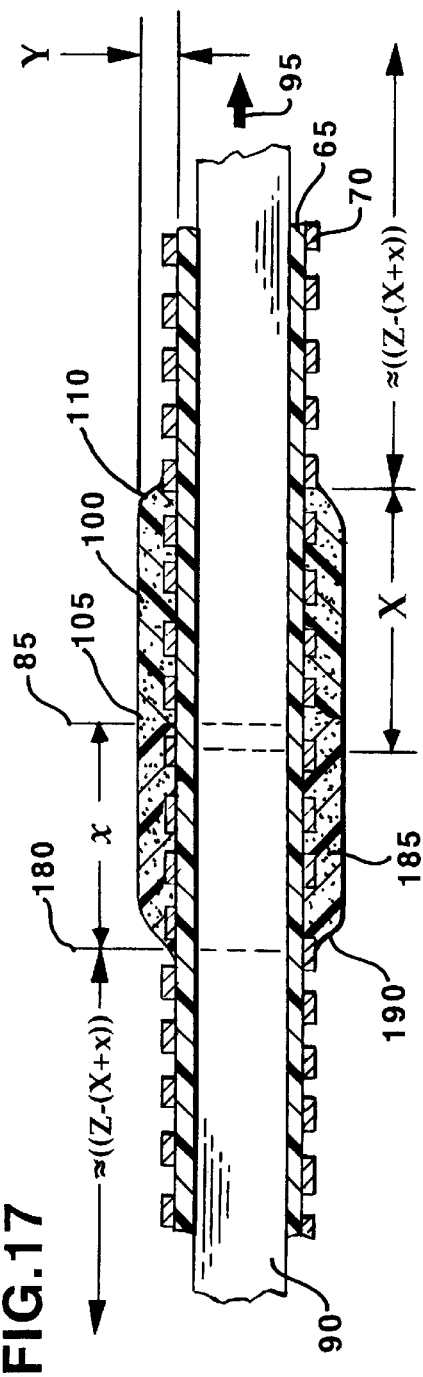

A first fabrication method is set forth in the flow chart of FIG. 16 and illustrated in FIGS. 17–21 whereby the proximal, intermediate and distal outer layers 75, 175, and 80, respectively, are formed of materials of different durometer hardness overlying the reinforcement layer 70 that extends the full length "Z" of the catheter body 15'. Steps S400–S404 are the same as steps S200–S204 of FIG. 3, resulting in the initial layer segment 100 illustrated in FIG. 4. In step S406, illustrated in FIG. 17, the intermediate segment layer 185 of thickness "Y" is extruded or molded over a length "x" of the reinforcement layer 70 proximal to the initial layer segment 100 such that it extends from the intermediate segment layer proximal end 190 into overlying contact with the tapered initial layer segment proximal end 105 of the initial segment layer 100. Because of this overlap, the lengths "x" and "X" overlap by a distance "Δ", and the distance along the exposed reinforcement layer 70 between the contiguously molded distal and intermediate segment layers 100 and 185 is approximately ("Z"–("X+x")). It should be noted that the order of steps S404 and S406 can be reversed or that both steps can be performed in a single molding or co-extrusion operation.

Figure 18:
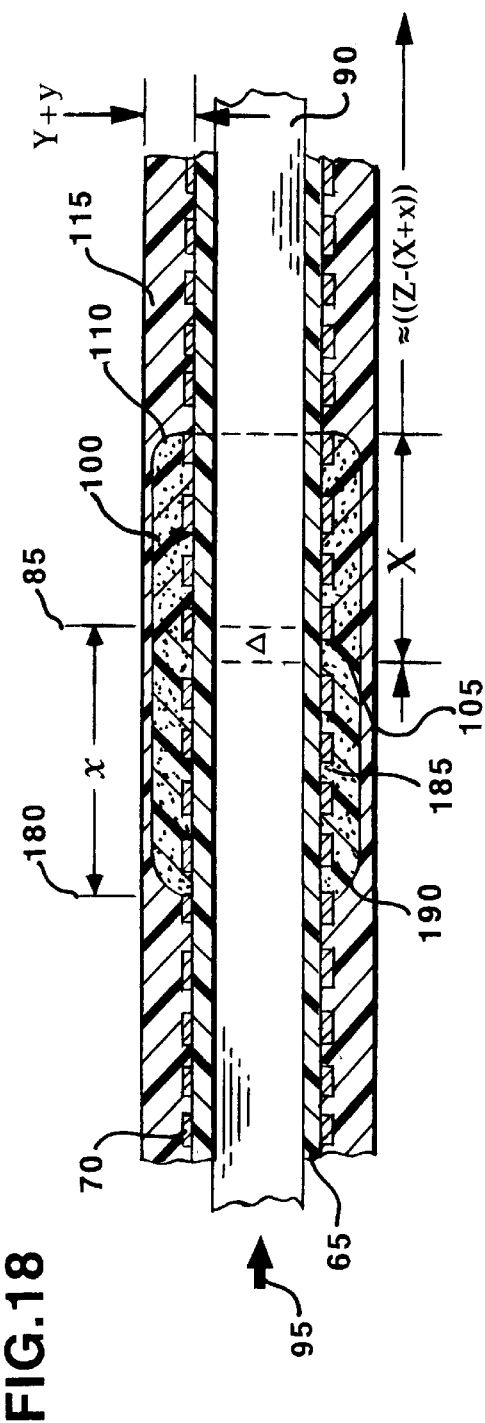
Figure 21:
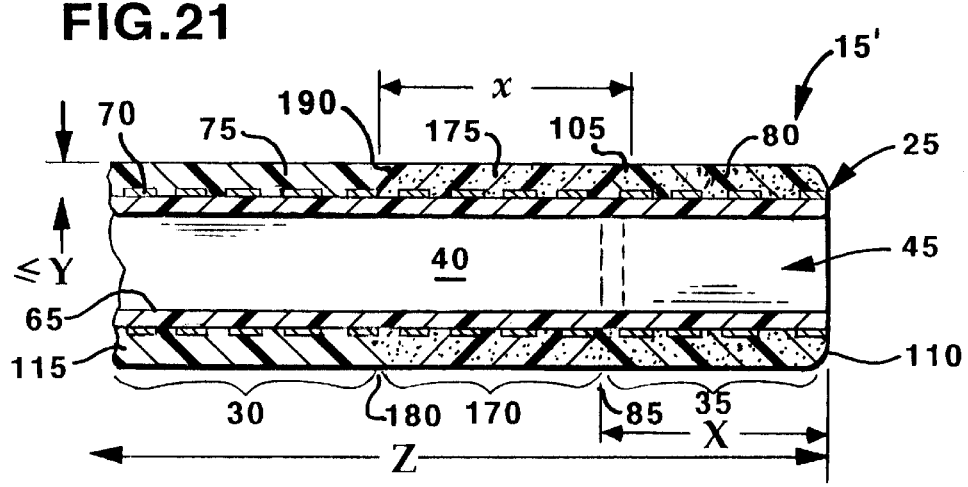

Step S408 illustrated in FIG. 18 is performed in substantially the same manner as step S206 described above. Steps S410 and S412, illustrated in FIGS. 19 and 20, respectively, are performed in substantially the same manner as steps S210 and S208, respectively, described above. However, the steps are reversed in order so that the catheter body outer layer is ground to the thickness ≦"Y" before the continuous catheter body tubing is cut along cut lines 125 into catheter body lengths. This reversal of these steps simply illustrates this possible order for each of the methods of the invention, and it will be understood that the order can be reversed in the practice of the method illustrated in FIG. 16. Finally, step S414 corresponds to step S212 to form the three section catheter 10' of FIG. 15. FIG. 21 illustrates the resulting distal segment of the catheter body 10' comprising the distal catheter section 35, the intermediate catheter section 170 and a distal portion of the proximal catheter section 30. It will be understood that the lengths "X" and "x" are not necessarily to scale and can be substantially longer or shorter than illustrated depending on the intended use and characteristics of the catheter body 15'. The discrete distal soft tip 145 of FIG. 8 can also be attached to form the distal catheter body end 25 as described above with respect to FIG. 8.

Figure 10:
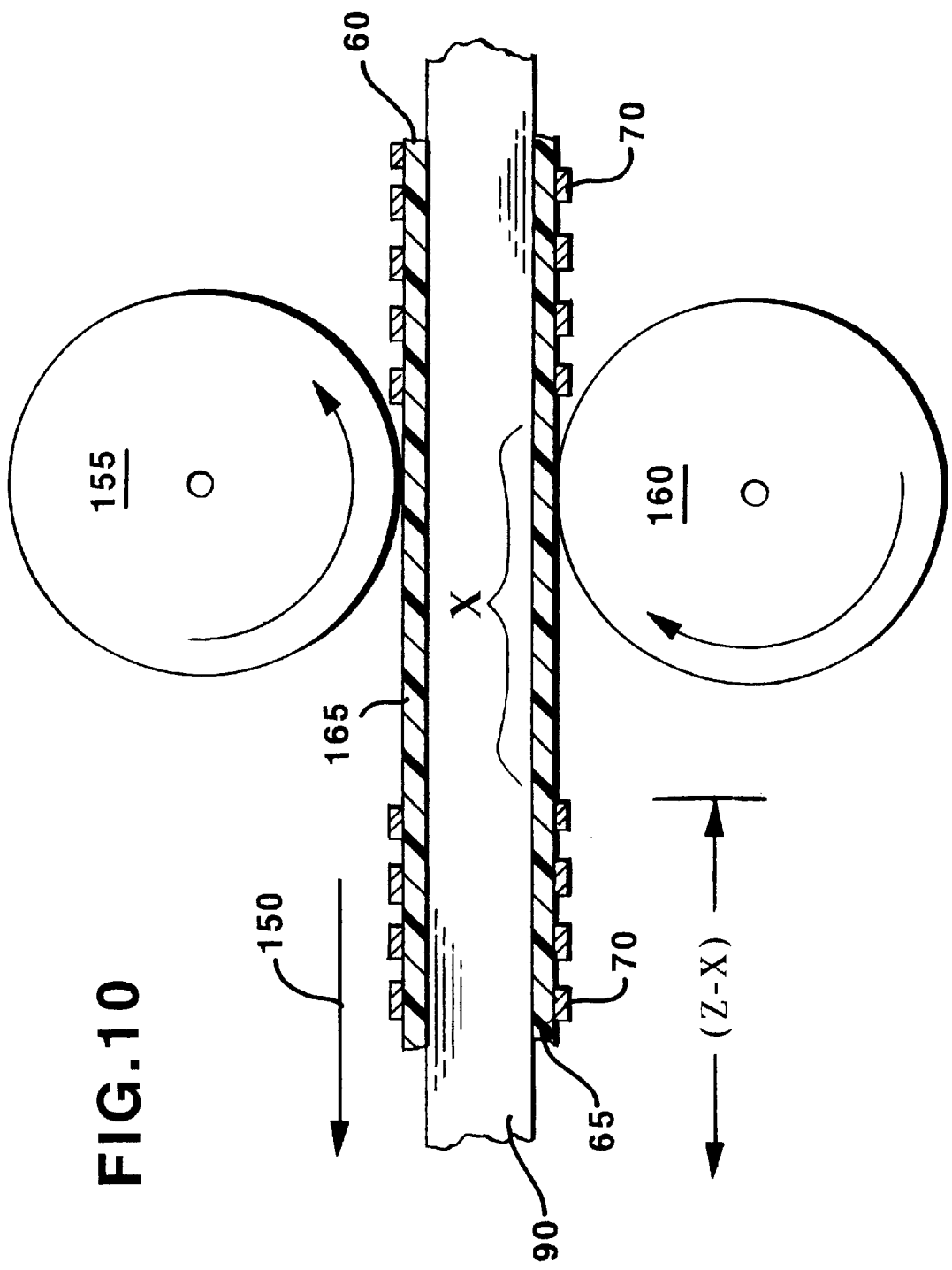

The method of FIGS. 16–21 can also be altered by the addition of the step S304 of FIG. 9, to remove the reinforcement layer 70 through the distal section length "X" to provide the exposed inner liner surface segment 165 illustrated in FIG. 10. This method is set forth in FIG. 22 where steps S500–S504 are the same as steps S300–S304 of FIG. 9 and illustrated in FIG. 10. In step S506, the initial layer segment of thickness "Y" is extruded or molded over a length "x" of the reinforcement layer 70 proximal to the exposed inner layer liner segments and over the length "X" of the exposed inner layer liner segment. Steps S508–S514 correspond to steps S408–S414 of FIG. 16. Thus, only two materials of differing durometer hardness are employed, and the three catheter sections differ in flexibility due to the underlying reinforcement layer in the intermediate catheter section of length "x". As shown in view of the resulting distal catheter body segment of FIG. 23, the reinforcement layer 70 is terminated at the distal junction 85. The distal outer layer 80 overlying the exposed inner liner surface of the distal catheter section length "X" and the intermediate outer layer 175 overlying the reinforcement layer 70 within the intermediate catheter section length "x" are formed at the same time of the continuous initial layer segment of a material of first hardness. The distal catheter section 35 is therefore more flexible than the reinforced intermediate catheter section 170. The proximal outer layer 75 is then formed as a final layer 115 of a material of second hardness, preferably of a greater durometer hardness than the durometer hardness of the initial layer segment. Consequently, the proximal catheter section 30 is less flexible than the intermediate catheter section 170 and the distal catheter section 35.

Figure 25:
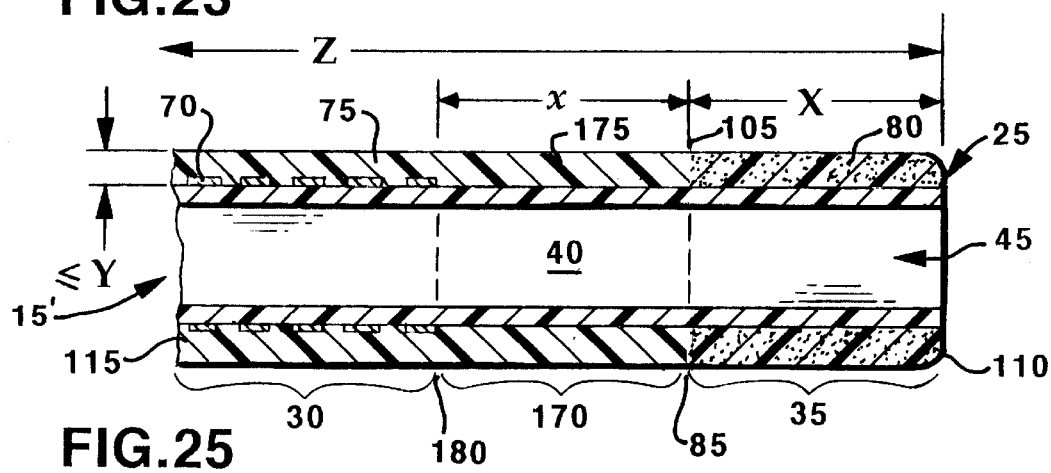
FIG. 25 is a partial cross-section view of a catheter body distal portion formed in accordance with the: method of FIG. 24.
Figure 24:
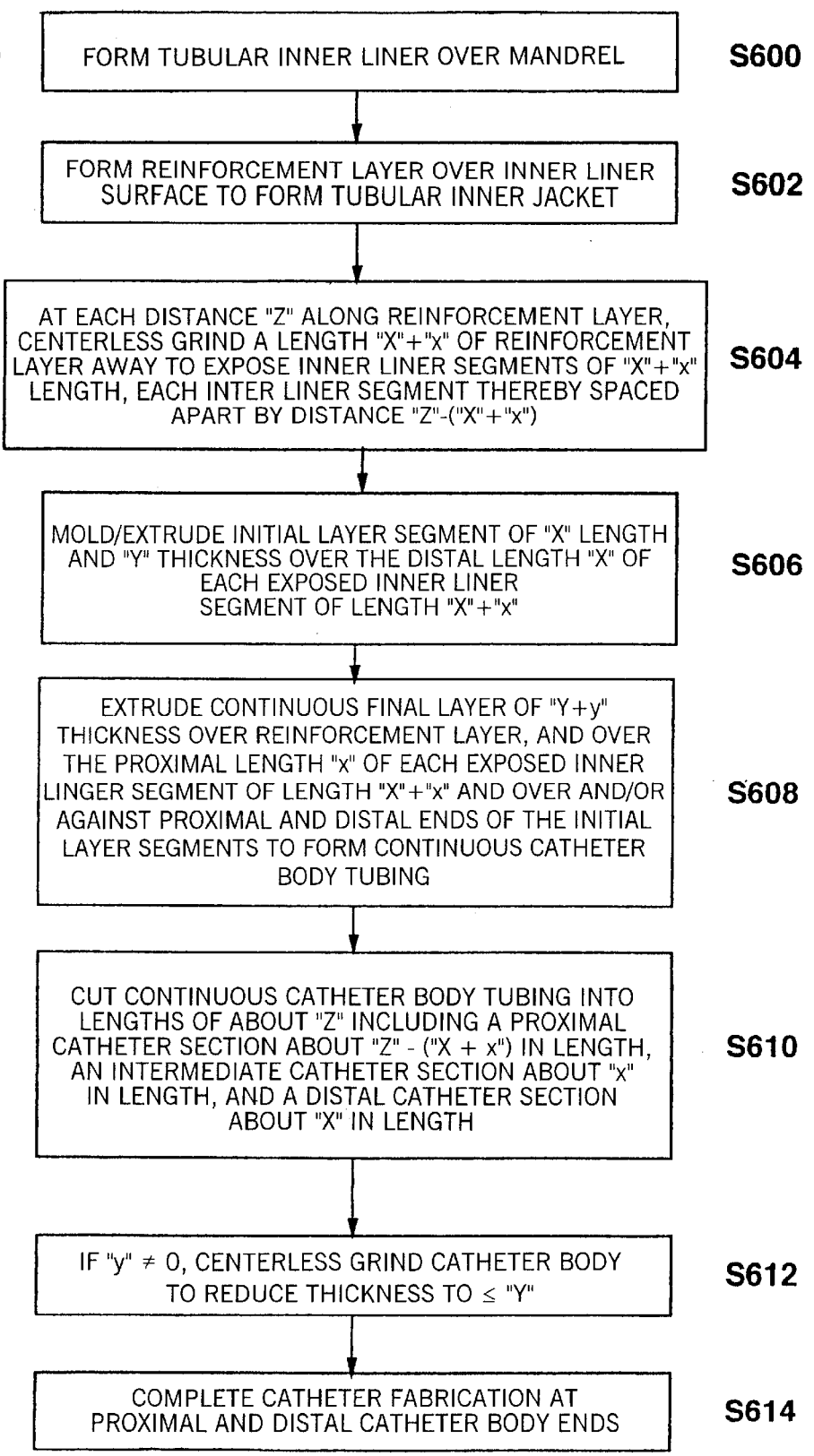
FIG. 24 is a flow chart of a further simplified fabrication process for forming a catheter of the type depicted in FIG. 15.

FIG. 24 sets forth the alternative approach of removing lengths "X"+"x" of the reinforcement layer 70, applying the initial layer segment 100 only over the length "X", and applying the final layer 115 over the reinforcement layer 70 and the remaining length "x" of the exposed inner liner surface segment. The resulting distal end segment of the catheter body 15' is shown in FIG. 25. Steps S600–S602 are the same as the first two steps of FIGS. 3, 9, 16 and 22. In step S604, the reinforcement layer is removed in the manner of step S304 of FIG. 9 as illustrated in FIG. 10, except that the removed length corresponds to the intended lengths of both the distal catheter segment and the intermediate catheter segment, that is a length "X" +"x". The separation distance between adjacent exposed inner liner segments of length "X"+"x" is "Z"–("X"+"x"). In step S606, the initial layer segment of thickness "Y" is extruded or molded only over the length "X" of the exposed inner layer liner segment. In step S608, the final layer segment is applied or formed over the reinforcement layer and the length "x" of the exposed inner liner surface segment between the adjacent initial layer segments. Steps S610–S614 correspond to the final three steps of each of the methods depicted in FIGS. 3, 9, 16, and 22. In this method depicted in FIG. 24, only two materials of differing durometer hardness are employed, and the three catheter sections differ in flexibility due to the lack of the underlying reinforcement layer in the intermediate catheter section of length "x". The resulting distal end, segment of the catheter body 15' is shown in FIG. 25.

Figure 23:
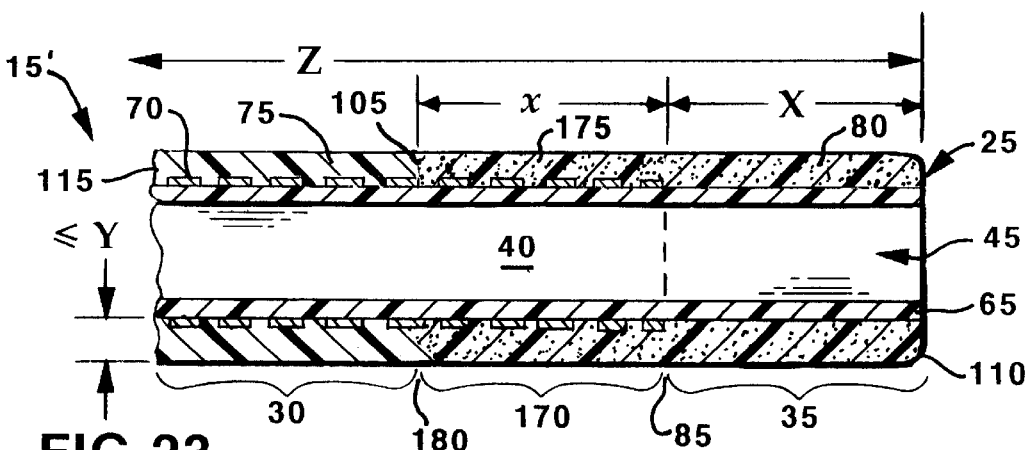
FIG. 23 is a partial cross-section view of a catheter body distal portion formed in accordance with the method of FIG. 22.

It will also be understood that the lengths "X" and "x" of the distal and intermediate catheter segments depicted in FIGS. 23 and 25 are not necessarily to scale and can be substantially longer or shorter than illustrated depending on the intended use and characteristics of the catheter body 15'. In each case, the discrete distal soft tip 145 of FIG. 8 can also be attached to form the distal catheter body end 25 as described above with respect to FIG. 8.

The steps of the methods of FIGS. 16, 22, and 24 can be selectively combined using three materials of differing durometer hardness applied in an initial segment layer and an intermediate segment layer and a final layer over selected lengths of exposed inner liner surface segments to create a catheter body of four catheter sections.

In all of the above-described methods, the first material (and the intermediate material, if present) is preferably molded over the continuous catheter body tubing in a cylinder, although it may be molded in a linear band, e.g., as a half cylinder section along the length "Z". The second material is preferably molded as a cylinder over the tubular inner jacket along the separation distances "Z"–"X" and over the first layer segments (and intermediate segment layers, if present) to form a continuous, cylindrical, catheter body tubing.

In each case, where the thickness "y"≠0, the tubular catheter body outer layer is preferably centerless ground to grind away the thickness of the layers overlying the jacket to ≦"Y". The centerless grinding step provides a catheter body of uniform diameter over its length exposing the outer surface of the initial layer segment and any intermediate segment layers.

The catheter body sections can be fabricated in accordance with any of the above-described methods in any selected lengths. The distal catheter section formed by any of the above-described processes has a typical length in the range from about 0.1 cm to 10 cm depending on the nature and use of the catheter. If the distal catheter section constitutes a distal soft tip of a guide catheter or angiographic catheter, its length can be in the range of 0.05 cm to 0.4 cm and typically between about 0.1 cm to 0.25 cm long for example, after distal end trimming. The intermediate catheter section formed by any of the above-described processes can be of any length suitable for the application. In over-the-wire (OTW) or flow directed microcatheters, the intermediate catheter section length can be formed range of about 1.0 cm to 20.0 cm, or even longer, and the distal catheter section can be between 1.0–10.0 cm, preferably about 4.0 cm. In this way, up to three distinct regions of flexibility, tensile strength, column strength, and hoop strength may be provided in a small diameter catheter. In certain cases, the intermediate catheter section or the distal catheter section can be formed of a material that is loaded with a radiopaque material to form a radiopaque ring just at or proximal to the distal catheter end. The intermediate section length can in this case be about 0.1 cm to 1.0 cm to provide high definition of the location of the radiopaque ring.

The fabrication methods of the present invention are particularly useful for forming medical vascular catheters in a wide range catheter body lengths and outer diameters and a wide range of catheter sections and section lengths. Such catheters include relatively large diameter guiding catheters and angiography catheters and medical catheters used to access various body cavities, ducts, tracts and organs having catheter body outside diameters of 2.67 mm (8 F) to 4 mm (12 F) or more. The fabrication methods of the present invention, however, are not limited to such large diameter catheters, and will be useful for smaller diameter vascular catheters, preferably below 2.67 mm (8 F), and frequently as small as 1 mm (3 F), and below, such as those used in neurological diagnostic and interventional procedures. Such small diameter vascular catheters will also be useful for other procedures, such as gynecological procedures, cardiac procedures, general interventional radiology procedures, and the like, for access to the small vasculature as necessary.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

PART LIST FOR FIGS. 1–25 medical catheter 10
catheter body 15
proximal catheter body end 20
distal catheter body end 25
proximal catheter section 30
distal catheter section 35
catheter lumen 40
catheter lumen distal end opening 45
proximal connector 50
catheter lumen proximal end opening 55
tubular inner jacket 60
tubular inner liner 65
reinforcement layer 70
proximal outer layer 75
distal outer layer 80
junction 85
mandrel 90
advancement direction 95
initial layer segment 100
initial layer segment proximal end 105
initial layer segment distal end 110
final layer 115
catheter body cut lines 125
centerless grinding advancement direction 130
centerless grinding wheel 135, 140
discrete distal soft tip 145
centerless grinding advancement direction 150
centerless grinding wheel 155, 160
exposed inner liner surface segment 165
intermediate catheter section 170
intermediate outer layer 175
proximal junction 180
intermediate segment layer 185
intermediate segment layer proximal end 190

What is claimed is:

1. A method of fabricating medical catheter bodies of length "Z" from continuous catheter body tubing, comprising the steps of:

extruding a continuous inner jacket having an outer surface and a catheter lumen extending therethrough;

forming initial layer segments on the outer surface of the continuous inner jacket, each segment having a length "X" and a thickness "Y" and being separated by a length "Z–X" along the length of the continuous inner jacket, wherein the initial layer segments are formed of a first material;

subsequently forming a final layer of a second material having a thickness "Y+y" over at least a portion of the inner jacket, thereby forming a continuous catheter body tubing; and severing the continuous catheter body tubing into catheter bodies of length "Z", the catheter bodies each having a proximal portion and a distal portion, wherein the distal portion has a distal end, a distal outer layer, and a length of approximately "X", and wherein the distal portion is substantially formed of the first material.

2. The method of claim 1, wherein the first material is softer than the second material, such that the distal portion is more flexible than the proximal portion.

3. The method of claim 1, wherein the initial layer segments have tapered proximal ends and tapered distal ends, and wherein the final layer overlies at least a portion of the tapered proximal and distal ends of the initial layer segments.

4. The method of claim 1, wherein the continuous inner jacket is formed of a lubricious material.

5. The method of claim 1, wherein the distal outer layer of the distal portion is formed of the first material.

6. The method of claim 1, further comprising the steps of:

forming a distal soft tip segment; and attaching the distal soft tip segment to the distal end of the distal portion of each catheter body.

7. The method of claim 1, wherein the step of forming initial layer segments further comprises the step of forming the initial layer segments as linear lines of thickness "Y" and length "X" along at least a portion of the inner jacket, thereby leaving the remaining portion of the inner jacket exposed;

and wherein the step of forming the final layer further comprises the step of forming the final layer over the exposed portion of the inner jacket and along the linear lines of the initial layer segments.

8. The method of claim 1, wherein the step of forming a continuous inner jacket further comprises the step of:

forming a reinforcement layer overlying the outer surface of the continuous inner jacket.

9. The method of claim 8, wherein the reinforcement layer is a wire braid.

10. A method of fabricating medical catheter bodies of length "Z" from continuous catheter body tubing, comprising the steps of:

extruding a continuous inner jacket having an outer surface and a catheter lumen extending therethrough;

forming initial layer segments on the outer surface of the continuous inner jacket, each initial layer segment having a length "X" and a thickness "Y" and being separated by a length "Z–X" along the length of the continuous inner jacket, wherein the initial layer segments are formed of a first material;

subsequently forming intermediate layer segments adjoining the initial layer segments along the length of the continuous inner jacket, each intermediate layer segment having a length "x" such that the contiguously formed initial and intermediate layer segments are separated by a length of approximately "Z–(X+x)", wherein the intermediate layer segments are formed of an intermediate material;

thereafter forming a final layer of a second material and having a thickness "Y+y" over at least a portion of the inner jacket, thereby forming a continuous catheter body tubing; and severing the continuous catheter body tubing into catheter bodies of length "Z", the catheter bodies each having a proximal portion, an intermediate portion and a distal portion, wherein the distal portion has a distal end, a distal outer layer, and a length of approximately "X", and wherein the distal portion is substantially formed of the first material.

11. The method of claim 10, wherein the hardness of the first material is less than the hardness of the second material, such that the distal portion is more flexible than the proximal portion.

12. The method of claim 11, wherein the hardness of the intermediate material is different from both the hardness of the first material and the hardness of the second material.

13. The method of claim 10, wherein the initial layer segments have tapered proximal ends and tapered distal ends, and wherein the final layer overlies at least a portion of the tapered distal end of each initial layer segment, and wherein each intermediate layer segment overlies at least a portion of the proximal end of each initial layer segment.

14. The method of claim 10, wherein the continuous inner jacket is formed of a lubricious material.

15. The method of claim 10, wherein the distal outer layer of the distal portion is formed of the first material.

16. The method of claim 10, further comprising the steps of:

forming a distal soft tip segment; and attaching the distal soft tip segment to the distal end of the distal portion of each catheter body.

17. The method of claim 10, wherein the step of forming initial layer segments further comprises the step of forming the initial layer segments as linear lines of thickness "Y" and length "X" along at least a portion of the inner jacket, thereby leaving the remaining portion of the inner jacket exposed;

and wherein the step of forming the final layer further comprises the step of forming the final layer over the exposed portion of the inner jacket and along the linear lines of the initial layer segments.

18. The method of claim 10, wherein the step of forming a continuous inner jacket further comprises the step of:

forming a reinforcement layer overlying the outer surface of the continuous inner jacket.

19. The method of claim 18, wherein the reinforcement layer is a wire braid.

20. A method of fabricating medical catheter bodies of length "Z" from continuous catheter body tubing, comprising the steps of:

extruding a continuous inner jacket having an outer surface and a catheter lumen extending therethrough;

forming initial layer segments on the outer surface of the continuous inner jacket, each initial layer segment having a length "X" and thickness "Y" and being separated by a length "Z–X" along the length of the continuous inner jacket, wherein the initial layer segments are formed of a first material;

subsequently forming a final layer of a second material and having a thickness "Y+y" over at least a portion of the inner jacket, thereby forming a continuous catheter body tubing; and severing the continuous catheter body tubing into catheter bodies of length "Z", the catheter bodies each having a proximal portion and a distal portion, wherein the distal portion has a distal end, and a distal outer layer formed of the first material.

21. The method of claim 20, wherein the first material is softer than the second material, such that the distal portion is more flexible than the proximal portion.

22. The method of claim 20, wherein the continuous inner jacket is formed of a lubricious material.

23. The method of claim 20, further comprising the steps of:
    forming a distal soft tip segment; and
    attaching the distal soft tip segment to the distal end of the distal portion of each catheter body.

24. The method of claim 20, wherein the step of forming a continuous inner jacket further comprises the step of:
    forming a reinforcement layer overlying the outer surface of the continuous inner jacket.

25. The method of claim 24, wherein the reinforcement layer is a wire braid.

* * * * *

UNITED STATES PATENT AND TRADEMARK OFFICE
CERTIFICATE OF CORRECTION

PATENT NO.   : 6,591,472 B1
DATED        : July 15, 2003
INVENTOR(S)  : Michael S. Noone, Albert H. Dunfee and Matthew S. Poole It is certified that error appears in the above-identified patent and that said Letters Patent is hereby corrected as shown below:

<u>Title page,</u>
Item [56], References Cited, U.S. PATENT DOCUMENTS, insert
-- 4,904,431A    2/1990    O'Maleki    264/103 --.

Signed and Sealed this

Fourth Day of May, 2004

JON W. DUDAS
*Acting Director of the United States Patent and Trademark Office*